US012688906B2

(12) United States Patent
Shah et al.

(10) Patent No.: US 12,688,906 B2
(45) Date of Patent: Jul. 21, 2026

(54) METHODS OF NORMALIZING AND CORRECTING RNA EXPRESSION DATA

(71) Applicant: TEMPUS AI, INC., Chicago, IL (US)

(72) Inventors: Kaanan Shah, Chicago, IL (US); Ashraf Hafez, Wheaton, IL (US); Catherine Igartua, Chicago, IL (US); Jackson Michuda, Chicago, IL (US)

(73) Assignee: TEMPUS AI, INC., Chicago, IL (US)

( * ) Notice: Subject to any disclaimer, the term of this patent is extended or adjusted under 35 U.S.C. 154(b) by 1154 days.

(21) Appl. No.: 16/581,706

(22) Filed: Sep. 24, 2019

(65) Prior Publication Data

US 2020/0098448 A1 Mar. 26, 2020

Related U.S. Application Data

(60) Provisional application No. 62/735,349, filed on Sep. 24, 2018.

(51) Int. Cl.
| | | |
|---|---|---|
| *G16B 30/00* | (2019.01) | |
| *G06F 16/215* | (2019.01) | |
| *G16B 5/00* | (2019.01) | |
| *G16B 40/10* | (2019.01) | |

(52) U.S. Cl.
CPC ........... *G16B 30/00* (2019.02); *G06F 16/215* (2019.01); *G16B 5/00* (2019.02); *G16B 40/10* (2019.02)

(58) Field of Classification Search
CPC .......... G16B 30/00; G16B 5/00; G16B 40/10; G16B 40/20; G16B 25/10; G06F 16/215
See application file for complete search history.

(56) References Cited

U.S. PATENT DOCUMENTS

| | | |
|---|---|---|
| 2014/0193818 A1 | 7/2014 | Rava et al. |
| 2014/0315199 A1 | 10/2014 | Rhodes et al. |
| 2015/0119262 A1 | 4/2015 | Scacheri |
| 2016/0186262 A1 | 6/2016 | Johnson |
| 2016/0224724 A1 | 8/2016 | Zhao et al. |
| 2016/0355806 A1 | 12/2016 | Lee et al. |
| 2018/0010136 A1 | 1/2018 | Hunt et al. |

OTHER PUBLICATIONS

Zheng, Wei et al. "Bias detection and correction in RNA-Sequencing data". BMC Bioformatics 2011 (Year: 2011).*
Wang, Qingguo et al. "Data Descriptor: Unifying cancer and normal RNA sequencing data from different sources" Scientific Data, Apr. 17, 2018 (Year: 2018).*

(Continued)

*Primary Examiner* — Karlheinz R. Skowronek
*Assistant Examiner* — Mary C Leverett
(74) *Attorney, Agent, or Firm* — MARSHALL, GERSTEIN & BORUN LLP

(57) ABSTRACT

A platform to perform normalization and correction on gene expression datasets and combines different datasets into a standard dataset using a framework configured to continuously incorporate new gene expression data. The framework determines a series of conversion factors that are used to on-board new gene expression datasets, such as unpaired datasets, where these conversion factors are able to correct for variations in data type, variations in gene expressions, and variations in collection systems.

16 Claims, 21 Drawing Sheets
(15 of 21 Drawing Sheet(s) Filed in Color)

100

(56) References Cited

OTHER PUBLICATIONS

Filloux, Cyril, et al. "An integrative method to normalize RNA-Seq data." BMC bioinformatics 15.1 (2014): 1-11. (Year: 2014).*

Anders, Simon, and Wolfgang Huber. "Differential expression analysis for sequence count data." Genome Biology 11.10 (2010): 1-12. (Year: 2010).*

Rozowsky, Joel, et al. "PeakSeq enables systematic scoring of ChIP-seq experiments relative to controls." Nature biotechnology 27.1 (2009): 66. (Year: 2009).*

Risso et al., GC-Content normalization for RNA-seq data, BMC Bioinformatics, 12(1):480 (Dec. 2011).

Ellis et al., RNA-seq optimization with eQTL gold standards, BMC Genomics, 1491):892 (Dec. 2013).

European Patent Application No. 19865279.4, Partial Supplementary European Search Report, dated Jun. 1, 2022.

Filloux et al., An integrative method to normalize RNA-Seq data, BMC Bioinformatics vol. 15, Article No. 188 (Jun. 14, 2014).

International Search Report and Written Opinion for Corresponding International Application No. PCT/US2019/052801, dated Jan. 28, 2020, 16 pages.

Johnson et al., Adjusting batch effects in microarray expression data using empirical Bayes methods, Biostatistics , 8(1), 118-127 (2007).

Leek et al., Capturing Heterogeneity in Gene Expression Studies by Surrogate Variable Analysis, PLoS Genet, 3 (9), 1724-1735 (2007).

Datta et al., Statistical Analysis of Next Generation Sequencing Data, (2014).

George et al., DAFS: a data-adaptive flag method for RNA-sequencing data to differentiate genes with low and high expression, BMC Bioinformatics, 15(1):92 (2014).

* cited by examiner

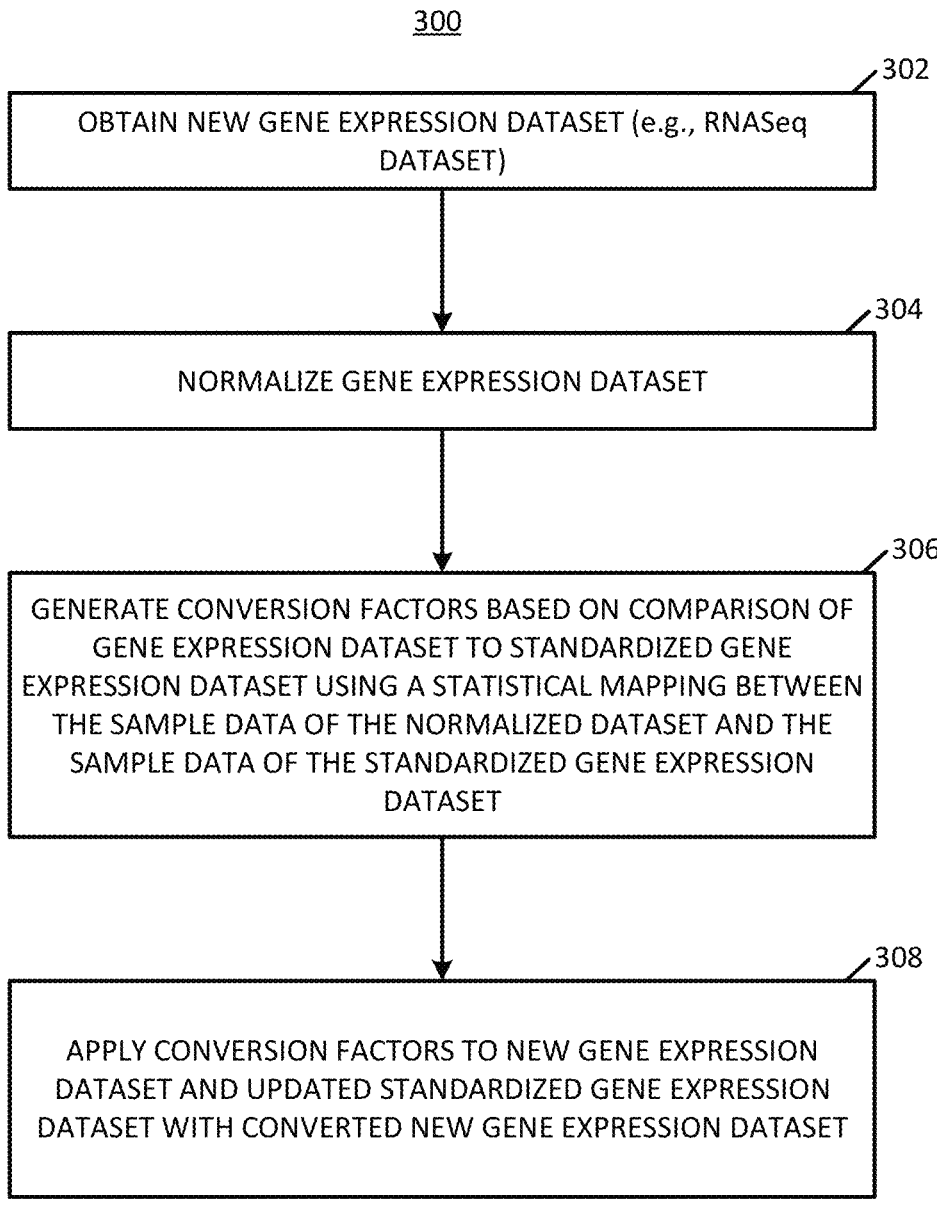

<u>300</u>

302

OBTAIN NEW GENE EXPRESSION DATASET (e.g., RNASeq DATASET)

304

NORMALIZE GENE EXPRESSION DATASET

306

GENERATE CONVERSION FACTORS BASED ON COMPARISON OF GENE EXPRESSION DATASET TO STANDARDIZED GENE EXPRESSION DATASET USING A STATISTICAL MAPPING BETWEEN THE SAMPLE DATA OF THE NORMALIZED DATASET AND THE SAMPLE DATA OF THE STANDARDIZED GENE EXPRESSION DATASET

308

APPLY CONVERSION FACTORS TO NEW GENE EXPRESSION DATASET AND UPDATED STANDARDIZED GENE EXPRESSION DATASET WITH CONVERTED NEW GENE EXPRESSION DATASET

*FIG. 3*

External Expression Dataset

IDENTIFICATION OF PCA OUTLIERS

METHODS OF NORMALIZING AND CORRECTING RNA EXPRESSION DATA

CROSS-REFERENCE TO RELATED APPLICATIONS

This application claims benefit of priority to and claims under 35 U.S.C. § 119(e)(1) the benefit of the filing date of U.S. provisional application Ser. No. 62/735,349 filed Sep. 24, 2018, the entire disclosure of which is incorporated herein by reference.

FIELD OF THE INVENTION

The present disclosure relates to normalizing and correcting gene expression data and, more particularly, to normalizing and correcting gene expression data across varied gene expression databases.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Experiments examining gene expression are valuable in assessing patient response and projected responses to various treatments. There are relatively large databases of gene expression data, such as The Cancer Genome Atlas (TCGA) project database, the Genotype-Tissue Expression (GTEx) project database, and others. Unfortunately, gene expression data, in particular from RNA sequencing experiments, can be highly sensitive to biases in sample type, sample preparation, and sequencing protocol. The result is gene expression data across databases and data sets that cannot be readily compared, and certainly not if a relatively high level of specificity and sensitivity is required for data analysis. As such, there is a desire for techniques to combine data across gene expression datasets to provide functionally useful and comparable gene expression data.

For gene expression data in the form of RNA sequencing data (referred to herein as "RNA seq" or "RNAseq" data), for example, main sources of bias are varied. Biases arise from tissue type (e.g., fresh frozen (FF) or formalin fixed, paraffin embedded (FFPE)), and RNA selection method (e.g., exon capture or poly-A RNA selection). For datasets sequenced using exome capture, for example, subtle differences between the different exome capture kits arise upon careful inspection. Examining these biases across multiple RNA seq datasets, it becomes clear that synchronizing RNA seq data is exceedingly challenging.

SUMMARY OF THE INVENTION

The present application presents techniques for normalizing and correcting gene expression data across varied gene expression databases.

In exemplary embodiments, techniques are provided for normalizing RNA sequence data and for correcting RNA sequence data to establish a uniform gene expression database. The techniques further provide for on-boarding new gene expression data into the uniform gene expression database enriching the new gene expression data for better utilization with existing gene expression data.

Such techniques provide numerous advantages, including unifying actual gene expression data and parsing that data into different tumor profiles to allow for more accurate analysis of gene expression data, including, for example, greatly reducing database access speeds and data processing times. The present techniques can combine data across gene expression datasets to provide functionally useful and comparable gene expression data that have heretofore been unavailable.

In accordance with an example, a computer-implemented method includes: generating, from a comparison of a normalized RNA sequence dataset against a standard RNA sequence dataset, at least one conversion factor for applying to a next RNA sequence dataset; and correcting RNA sequence data of the next RNA sequence dataset using the at least one conversion factor.

In some examples, the computer-implemented method further includes: including the RNA sequence data of the next gene expression dataset into the standard gene expression dataset.

In some examples, the computer-implemented method includes: obtaining a gene expression dataset comprising the RNA sequence data for one or more genes, normalizing the RNA sequence data using gene length data, guanine-cytosine (GC) content data, and depth of sequencing data; and performing a correction on the RNA sequence data against the standard gene expression dataset by comparing the sequence data for at least one gene in the gene expression dataset to sequence data in the standard gene expression dataset.

In some examples, such normalization is performed by normalizing the gene length data for at least one gene to reduce systematic bias, normalizing the GC content data for the at least one gene to reduce systematic bias, and normalizing the depth of sequencing data for each sample.

In some examples, generating the at least one conversion factor includes: for a sample gene, obtaining sample data from the normalized dataset and obtaining sample data from the standard gene expression dataset; determining a statistical mapping between the sample data of the normalized dataset and the sample data of the standard gene expression dataset; and determining the at least one conversion factor using the statistical mapping.

In some examples, determining the statistical mapping includes determining a linear mapping model between the sample data of the normalized dataset and the sample data of the standard gene expression dataset.

In some examples, the computer-implemented method includes: determining an intercept and a beta value for the linear mapping model; and determining the at least one conversion factor using the statistical mapping from the intercept and the beta value.

In accordance with another example, a computing device comprising one or more memories and one or more processors is configured to: generate, from a normalization of an RNA sequence data against a standard RNA sequence dataset, at least one conversion factor for applying to a next RNA sequence dataset; and correct RNA sequence data of the next RNA sequence dataset using the at least one conversion factor.

In some examples, the computing device is configured to include the corrected RNA sequence data of the next RNA sequence dataset into the standard RNA sequence dataset.

In some examples, the computing device is configured to: obtain a gene expression dataset comprising the RNA sequence data for one or more genes, the RNA sequence data including gene length data, guanine-cytosine (GC) content data, and/or depth of sequencing data; and normalize the RNA sequence data to remove systematic known biases.

In some examples, the computing device is configured to: normalize the gene length data for the one or more genes to reduce systematic bias; normalize the GC content data for the one or more genes to reduce systematic bias; and normalize the depth of sequencing data for the RNA sequence data.

In some examples, the computing device is configured to: for a sample gene, obtain sample data from a normalized RNA sequence dataset and obtaining sample data from the standard RNA sequence dataset; determine a statistical mapping between the sample data of the normalized RNA sequence dataset and the sample data of the standard RNA sequence dataset; and determine the at least one conversion factor using the statistical mapping.

In some examples, the computing device is configured to: determine an intercept and a beta value for the linear mapping model; and determine the at least one conversion factor using the statistical mapping from the intercept and the beta value.

In accordance with another example, a computer-implemented method includes: generating, from a normalization of gene expression data against another gene expression dataset, at least one conversion factor for applying to a next gene expression dataset; and correcting gene sequence data of the next gene expression dataset using the at least one conversion factor.

In accordance with an example, a computer-implemented method comprises: receiving, at one or more processors, a gene expression dataset; identifying within the gene expression dataset, using a regression technique implemented by the one or more processors, gene expression data having multiple modal expression peaks; for the gene expression data, normalizing, using the one or more processors, a spacing between each of the multiple model expression peaks to form a normalized gene expression data; and storing the normalized gene expression data in a normalized gene expression dataset.

In accordance with another example, a computer-implemented method comprises: receiving, at one or more processors, a RNA sequence dataset; identifying within the gene expression dataset, using a regression technique implemented by the one or more processors, a plurality of RNA expression data each having a bimodal distribution comprising two expression peaks; for each of the plurality of RNA expression data, normalizing, using the one or more processors, a spacing between the two expression peaks such that each of the plurality of RNA expression data has the same spacing between the two expression peaks; and storing the normalized RNA expression data in a normalized RNA sequence dataset.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the neccessary fee.

The figures described below depict various aspects of the system and methods disclosed herein. It should be understood that each figure depicts an example of aspects of the present systems and methods.

FIG. 3 is a block diagram of an example process for updating a standard gene expression dataset with new gene expression data using one or more conversion factors, in accordance with an example.

DETAILED DESCRIPTION

Figure 1:
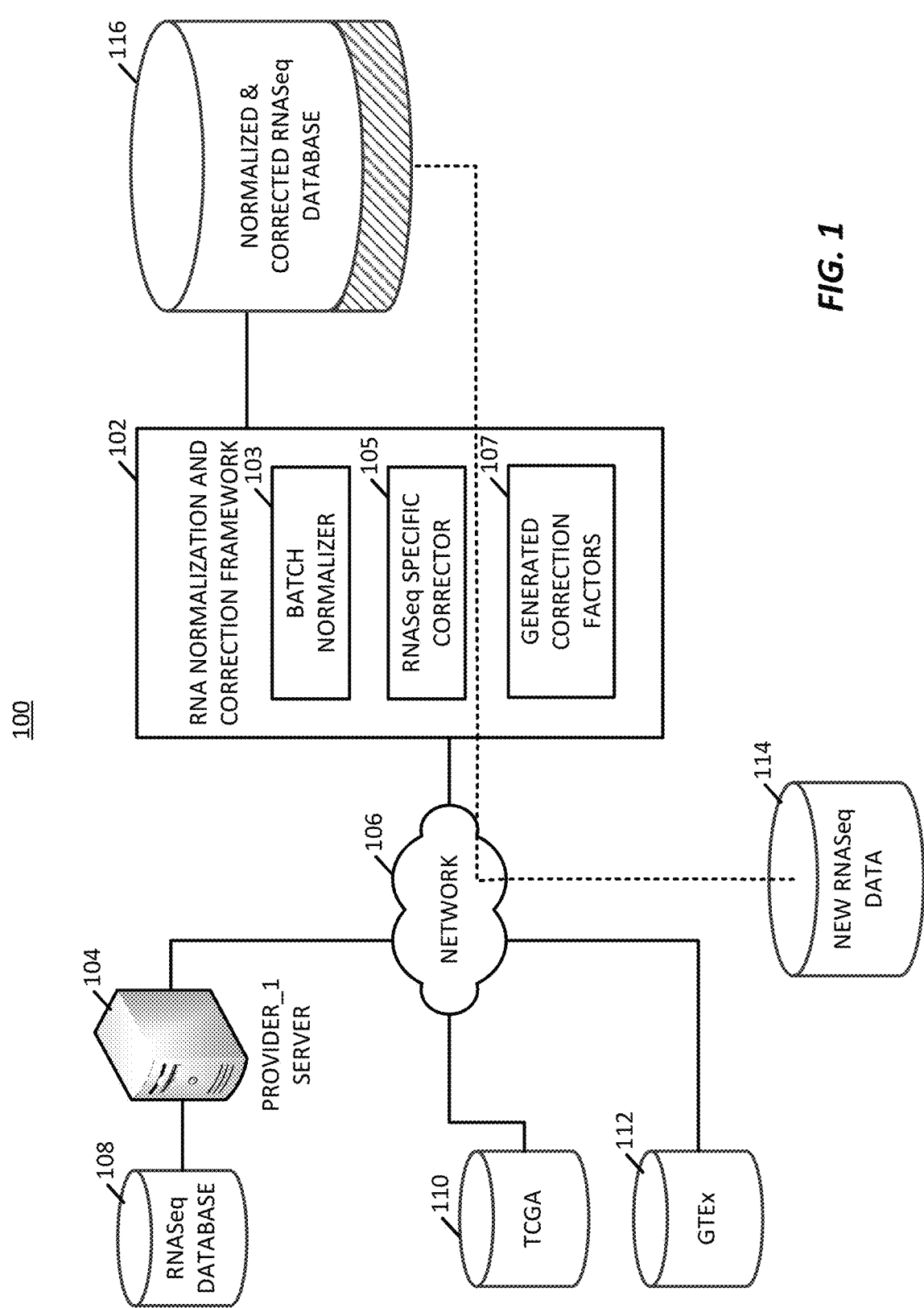
FIG. 1 is a schematic illustration of an example computer processing system for normalizing and correcting RNA expression data, in accordance with an example.

The present application presents a platform for performing normalization and correction on gene expression datasets to allow for combining of different datasets into a standardized dataset, such as a previously normalized dataset, that may continuously incorporate new data. The present techniques generate a series of conversion factors that are used to on-board new gene expression datasets, such as unpaired datasets, where these conversion factors are able to correct for variations in data type, variations in gene expressions, and variations in collection systems. For example, conversion factors are able to correct against data collection bias, variations in laboratory data generation processes, variations in data sample size, and other factors that can cause incongruity between datasets. The techniques may correct older datasets for inclusion into new dataset. For example, existing, stable datasets, such as the TCGA (on the world wide web at portal.gdc.cancer.gov)) or GTEx (on the world wide web at gtexportal.org/home), may be corrected to match new datasets. Examples of RNA seq datasets include RNAseq data from FFPE tissue, RNAseq data from fresh frozen tissue, or from other tissue from which RNA seq data may be extracted. Datasets may come from laboratories, from individual research institutions, from public data repositories such as TCGA and GTEx, or from other sources.

The present techniques include platforms for normalization of gene expression data, such as RNA sequence data or array-based technologies data, and comparison of gene expression data to a standard gene expression dataset. The present techniques include platforms for generating one or more conversion factors by comparing gene expression data to such standard gene expression datasets. The present techniques include correcting gene expression data, such as RNA sequence data, of subsequent gene expression datasets using these one or more conversion factors, thereby allowing subsequent gene expression datasets to be integrated into the standard gene expression dataset.

In some examples, the present techniques include obtaining a gene expression dataset having RNA sequence data for one or more genes, where that RNA sequence data includes gene length data, guanine-cytosine (GC) content data, and depth of sequencing data. In other examples, other types of gene expression datasets from array-based technologies, such as RNA microarrays, may be obtained. The techniques may include performing normalization of the RNA sequence data or other gene expression datasets. The normalization may include normalizing the gene length data for at least one gene to reduce systematic bias, normalizing the GC content data for the at least one gene to reduce systematic bias, and normalizing the depth of sequencing data for each sample, for example. The normalized dataset may be compared against the standard gene expression dataset by comparing the sequence data for at least one gene in the gene expression dataset to sequence data in the standard gene expression dataset to generate at least one conversion factor.

FIG. 1 illustrates a system 100 for normalizing and correcting gene expression data, such as RNA seq data. A normalization and correction framework 102 is coupled to receive gene expression data from a multitude of different sources through a communication network 106. The framework 102, for example, may be coupled to a health care provider computing system 104, such as a research institution computing system, lab computing system, hospital computing system, physician group computing system, etc., that makes available stored gene expression data in the form of RNA sequencing dataset 108. Other gene expression network-accessible datasets are also coupled to the network 106, including the Cancer Genome Atlas (TCGA) dataset 110 and the Genotype-Tissue Expression (GTEx) dataset 112, both examples of established gene expression datasets that can be normalized and corrected to be incorporated into a already-normalized and corrected growing database of gene expression data.

The framework 102 includes a batch normalizer 103 configured to perform gene expression batch normalization processes in accordance with examples herein, processes that adjust for known biases within the dataset including, but not limited to, GC content biases, gene length biases, and sequencing depth biases. In the example of FIG. 1, the framework 102 is further configured to perform gene expression correction processes in accordance with examples herein using a RNA seq corrector 105. As discussed herein, the processes of the normalizer 103 and the corrector 105 are used by the framework 102 to normalize gene expression data and generate one or more correction factors (107), which are stored in the framework 102 and applied by the framework 102 to convert new gene expression datasets, such as dataset 114. Applying these correction factors to the new dataset 114, for example, the framework 102 is able to normalize, correct, and convert that dataset 114 into a format for integration into an existing normalized, corrected gene expression dataset 116, as shown.

The framework 102 may be implemented on a computing device such as a computer, tablet or other mobile computing device, or server. The framework 102 may be implemented by any number of processors, controllers or other electronic components for processing or facilitating the RNA sequencing data analyses. In some examples, the system 100 is implemented in a broader system that includes processing and hardware for imaging feature analysis, such as analyzing features in medical imaging data, immune infiltration data analysis, DNA sequencing data analysis, organoid development analysis, and/or other modality analyses.

Figure 2:
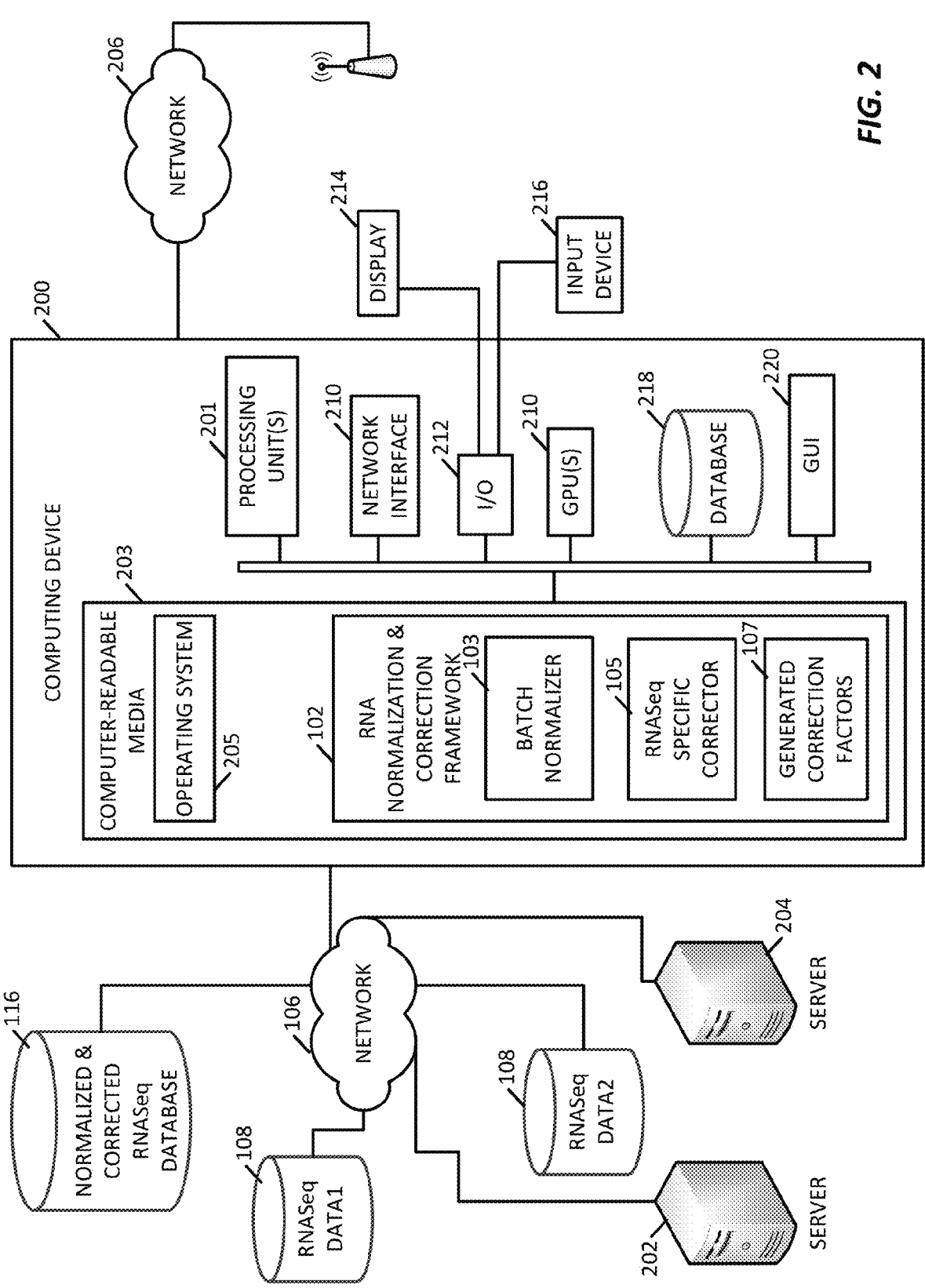
FIG. 2 illustrates an example computing device for implementing the systems of FIG. 1 and the processes of FIGS. 3-6, in accordance with an example.

An example computing device 200 for implementing the framework 102 is illustrated in FIG. 2. As illustrated, the framework 102 may be implemented on the computing device 200 and in particular on one or more processing units 201, which may represent Central Processing Units (CPUs), and/or on one or more or Graphical Processing Units (GPUs), including clusters of CPUs and/or GPUs. The framework 102 may be configured to perform processes of the techniques herein, such as those described with reference to FIGS. 3-9. Features and functions described for the framework 102 may be stored on and implemented from one or more non-transitory computer-readable media 203 of the computing device 200. The computer-readable media 203 may include, for example, an operating system 205 and the framework 102. More generally, the computer-readable media may store the batch normalizer 103 for executing batch normalization process instructions, a gene expression corrector (e.g., the RNASeq specific inspector 105) for executing gene expression process instructions, and the generated correction factors 107. The computing device 200 may be a distributed computing system, such as an Amazon Web Services cloud computing solution.

The computing device 200 includes a network interface 210 communicatively coupled to the network 106, for communicating to and/or from a portable personal computer, smart phone, electronic document, tablet, and/or desktop personal computer, or other computing devices. The computing device further includes an I/O interface 212 connected to devices, such as digital displays 214, user input devices 216, etc. The computing device 200 may be connected to gene expression databases 108 through network 106, as well as the normalized and corrected gene expression database 116. In some examples. A database 218 within the computer device 200 may be used to store gene expression data, including new gene expression data for normalization and correction, normalized and corrected gene expression data, or other data. A graphic user interface (GUI) generator 220 is provided for generating digital reports, user interfaces, etc. for allowing users to interact with the normalized and corrected gene expression databases.

The functions of the framework 102 may be implemented across distributed devices 202, 204, etc. connected to one another through a communication link. In other examples, functionality of the system 100 may be distributed across any number of devices, including the portable personal computer, smart phone, electronic document, tablet, and desktop personal computer devices shown. The server 200 may be communicatively coupled to the network 106 and another network 206. The networks 106/206 may be public networks such as the Internet, a private network such as that of research institution or a corporation, or any combination thereof. Networks can include, local area network (LAN), wide area network (WAN), cellular, satellite, or other network infrastructure, whether wireless or wired. The networks can utilize communications protocols, including packet-based and/or datagram-based protocols such as Internet protocol (IP), transmission control protocol (TCP), user datagram protocol (UDP), or other types of protocols. Moreover, the networks can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 200 may represent a CPU-type processing unit, a GPU-type processing unit, a field-programmable gate array (FPGA), another class of digital signal processor (DSP), or other hardware logic components that can be driven by a CPU.

FIG. 3 illustrates a process 300 that may be executed by the system 100. Gene expression data is obtained from a gene expression database or data source, at process 302. In the example of RNA seq data, the dataset may be obtained from a high throughput sequencer, such as Illumina HiSeq, Illumina NextSeq, Illumina NovaSeq, or other high throughput sequencing machines. The framework normalizes the newly obtained gene expression dataset, at process 304, to eliminate biases caused by, for example, GC content, gene length, and sequencing depth. Conversion factors are generated by comparing the obtained gene expression dataset to a standard gene expression dataset using a statistical mapping model, at process 306. Examples of statistical mapping model include, but are not limited to, a standard linear model, a generalized linear model (using for example a gamma distribution of counts data), or non-parametric methods, such as data transformation into ranks. The generated conversion factors are stored by the framework, as a result. At process 308, conversion factors are applied to the new gene expression data, which is then integrated into the standard dataset, in this converted form, at process 308.

Figure 4:
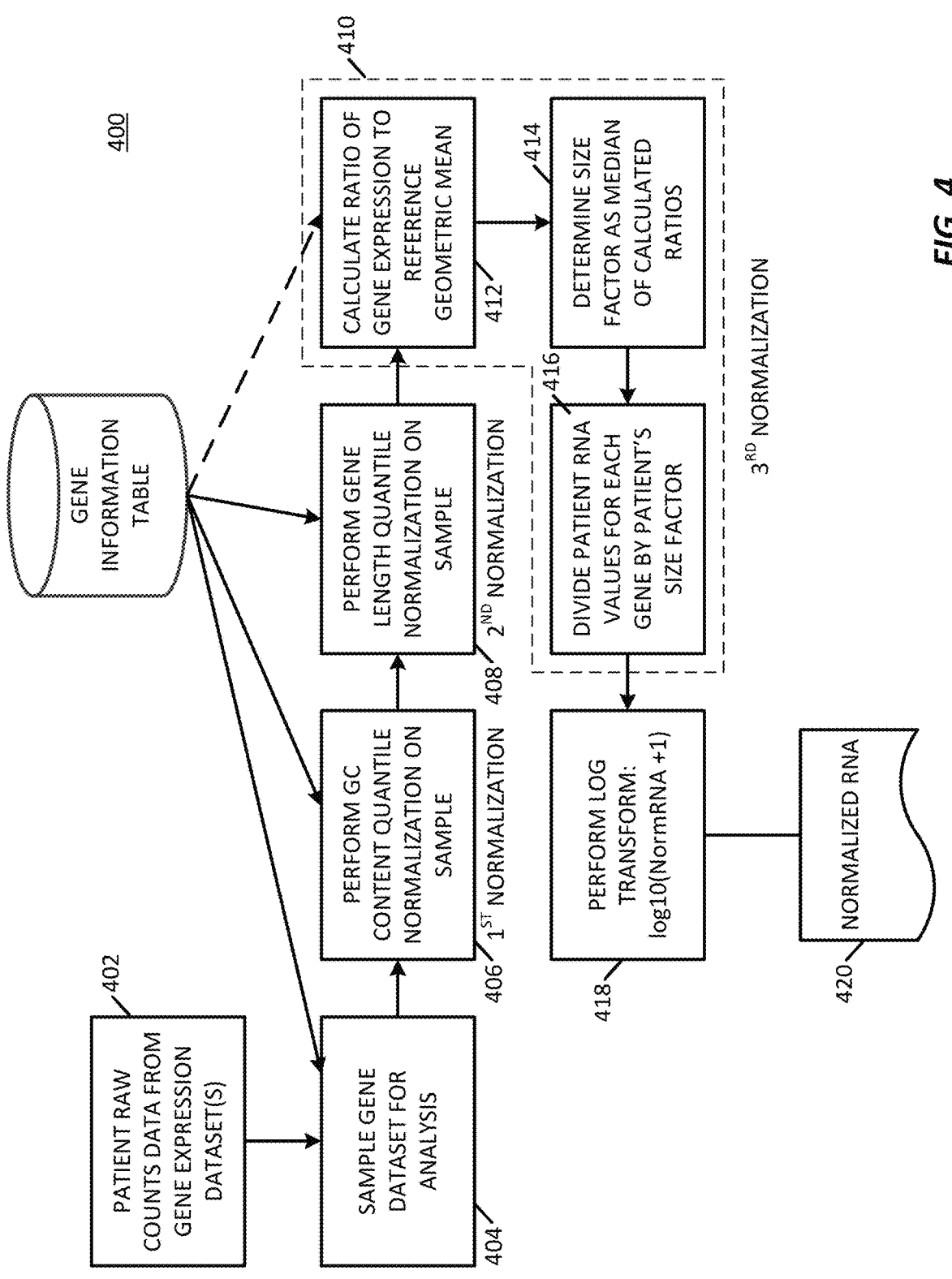
FIG. 4 is a block diagram of an example process for performing RNA seq normalization, as may be implemented by the process of FIG. 5, in accordance with an example.

FIG. 4 illustrates an example normalization process 400 to be applied to received raw gene expression data. A gene expression dataset is obtained, e.g., from a network accessible database connected to the network 106. The selection may be manual, by an operator using a graphical user interface provided to a display. The selection may be automated, such as when pre-determined search data is accessed by the system 100 and used to find corresponding data in the gene expression dataset (process 402). The gene expression dataset may contain RNA seq data, e.g., the TCGA, GTEx, or other database. The gene expression data may be array-based data, in other examples.

A gene information table comprising information such as gene name and starting and ending points (to calculate gene length) and gene GC content, is accessed and the resulting information is used to determine sample regions (process 404) for analyzing the gene expression datasets. A GC content normalization process 406 is performed using a first full quantile normalization process, e.g., a quantile normalization process like that of the R packages EDASeq and DESeq normalization processes (on the world wide web at bioconductor.org/packages/release/bioc/html/DESeq.html) may be used. In an example, a 10 quantile bin normalization is performed. The GC content for the sampled data is then normalized for the gene expression dataset. Subsequently, a second, full quantile normalization (e.g., using 10 quantile bins) is performed on the gene lengths in the sample data, at process 408.

To correct for sequencing depth, a third normalization process 410 may be used that allows for correction for overall differences in sequencing depth across samples, without being overly influenced by outlier gene expression values in any given sample. In exemplary embodiments, at a process 412, a global reference is determined by calculating a geometric mean of expressions for each gene across all samples. In other examples the reference geometric mean is obtained from the gene information table based on the existing datasets (e.g., GTEx, TCGA, etc.).

The size factor is used to adjust the sample to match the global reference. In operation, a sample's expression values are compared to a global reference geometric mean (process 412), creating a set of expression ratios for each gene (i.e., sample expression to global reference expression). At a process 414, a size factor is determined as the median value of these calculated ratios. The sample is then adjusted by the single size factor correction in order to match to the global reference, e.g., by dividing gene expression value for each gene by the sample's size factor, at a process 416.

In the illustrated example, after normalization, log transformation is performed on the RNA seq data for each gene, at a process 418. The entire GC normalized, gene length normalized, and sequence depth corrected RNA seq data is stored as normalized RNA seq data, at process 420.

Each of the normalizations for process 400 may be perform in sequential manner, where the output of one process provides input data to the next subsequent process. The particular ordering of the normalizations, however, is not important, as any of the three normalization processes may be performed in any order. Furthermore, alternative normalization methods can be applied, including but not limited to, Fragments Per Kilobase Million (FPKM), Reads Per Kilobase Million (RPKM), Transcripts Per Kilobase Million (TPM), and 3rd quartile normalization.

In some examples, an objective of the present techniques is to combine RNA seq data across many different datasets, overcoming the technical differences in sample collection methods used by many labs today. As noted above, different sources of bias can affect RNA seq datasets, these include biases based on tissue type, e.g., fresh, frozen or formalin fixed, paraffin embedded (FFPE). Other biases arise from selection method, e.g., exon capture or poly-A RNA selection. Even for datasets sequenced using exome capture, subtle differences between different exome capture kits can affect datasets.

In order to correct for these biases, the system 100 may perform a correction after normalization for samples sequenced and obtained from external sources, e.g., network accessible databases, 108, 110, 112, and 114, for example. For each of these different databases a per-gene correction factor may be developed so that samples across datasets can be compared and analyzed for correction and integration into a normalized, corrected gene expression dataset.

Figure 5:
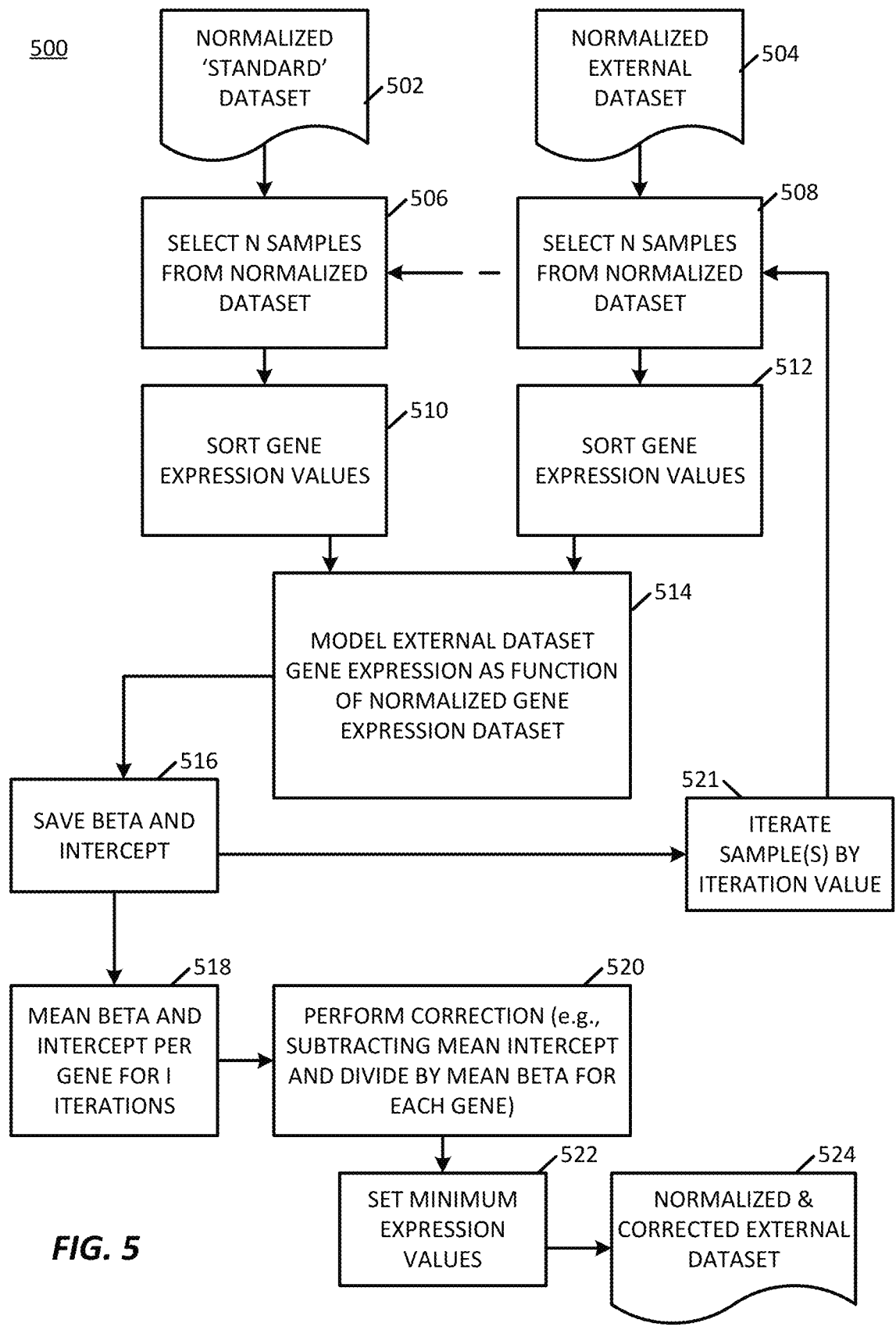
FIG. 5 is a block diagram of an example process for generating conversion factors and performing RNA seq correction on unpaired normalized RNA datasets, produced by the process of FIG. 4, in accordance with an example.

FIG. 5 illustrates an example correction process 500 to be applied to the normalized RNA seq data produced by the process 400. For the illustrated example, in order to calculate the per gene correction factors, an equal number of samples, N, was obtained from two datasets, the normalized gene expression dataset (502) from the process 400 and the standard dataset (504), also normalized from the process 400. The two datasets 502/504 may be sampled an equal number of times, at processes 506 and 508, respectively. The sampling may be over random locations within the datasets, or based on a plurality of meta-data elements, for example, by cancer type, tissue type, age, gender, etc. Sampling can be done for all genes or may be confined to gene expression data within certain ranges of data, such as for example over certain genes or collections of genes identified in the datasets. Further, the total sample sizes for each dataset may vary, but generally should be at least 30 samples in size.

In the illustrated example, for each sampled dataset for which there is no paired data, for each gene, gene expression values were sorted (510 and 512) based on numerical values and used to estimate a statistical mapping/statistical transformation model (at process 514), in the form of a linear transformation model, for each gene. A linear transformation model is an example, as other techniques may be used to model the new (external) dataset to the standard (internal) dataset.

In exemplary embodiments, the linear transformation model (514) converts data from one type of data to another. The linear transformations are performed for each sample mapping from one dataset to the other, and the corresponding intercept and beta values for each linear transformation are stored (at process 516). The sampling is repeated, e.g., 10, 100, 1000, or 10000 times (e.g., through an iterative process), and the corresponding intercept and beta values are determined, and the mean intercept and mean beta values are computed for the linear transformations (518).

The mean beta and intercept values are then stored (at process 518) as conversion factors that may be used to correct the normalized external dataset from process 400. For example, a process 520 may subtract the mean intercept from the gene expression values in the normalized external dataset and divide the gene expression values by the mean beta for each gene. The mean intercept and mean beta comes from taking the average of X number of sampling iterations (through iteration feedback 521), for example 100 iterations, to estimate the model. At a process 522, any gene expression value after correction, that is below 0, is set to that minimum, e.g., 0, since gene expression values are constrained to be non-negative. The resulting normalized and corrected external dataset (524) is produced and stored by the system 100, either separately or stored as part of the dataset 116, for example.

Figure 6:
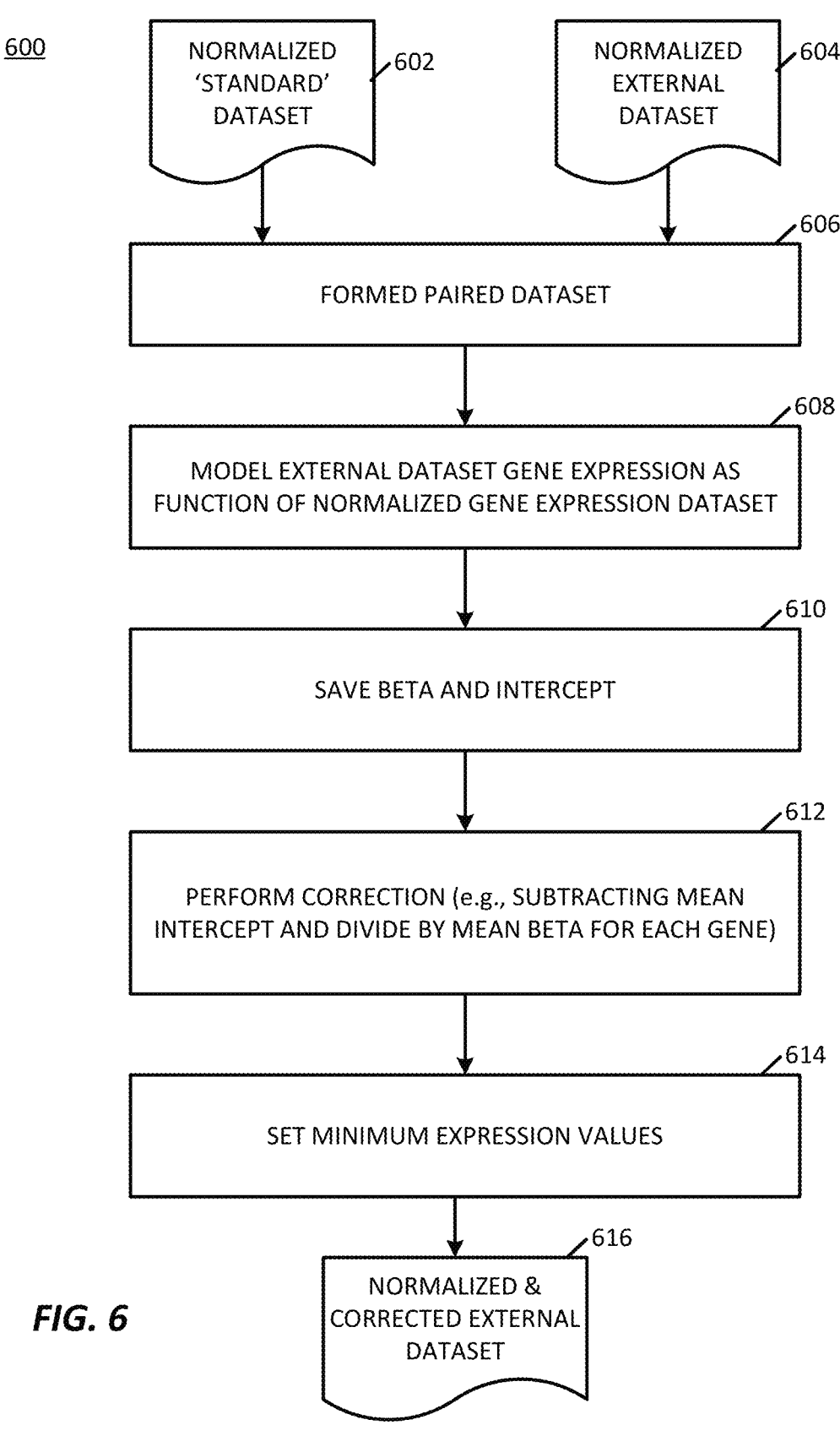
FIG. 6 is a block diagram of an example process for performing correction on a paired dataset formed from multiple normalized gene expression datasets, in accordance with an example.

FIG. 6 illustrates an example correction process 600 to be applied to the normalized RNA seq data produced by the process 400 for paired datasets. Two datasets 602 and 604 have been combined through a normalization process to form a paired dataset 606. An example of a paired dataset 606 would include, but is not limited to, data generated in the same manner as the standard dataset (602), and data, for the same set of samples, using a different data generation process (i.e. data generated using polyA-capture based RNA sequencing and exome-capture based RNA sequencing for the same set of samples). For the illustrated example, in order to calculate the per gene correction factors, a statistical mapping (610) would be created between the samples in the new RNA sequencing data (602) to the standard RNA sequencing data (602), using a model. The model parameters from the statistical mapping, e.g., the beta and intercept value, are obtained (612), stored as conversion factors, and used to correct the new RNA sequencing data, e.g., by subtracting the intercept value and dividing by the beta value. These conversion factors would be used to transform the new RNA sequencing dataset into the standard dataset and be deposited into the standard dataset database (614), in a similar manner to that of process 500, from minimum expression values, and a normalized and corrected dataset 616 is formed.

The normalized and corrected gene expression data may be provided as input data to any number of data analysis processes, data display processes, etc. The normalized and corrected gene expression data may be combined with additional types of data for such processes, as well. Examples of additional types of data that could be combined with the present application or be presented in addition to, include proteomics, metabolomics, metabonomics, epigenetics, microbiome, radiomics, and genomics data. Other examples may include non-molecular data such as clinical, epidemiological, demographic, etc. Proteomics data may comprise of protein expression, protein modifications, and protein interactions obtained from high-throughput proteomic technologies such as mass spectrometry-based tech or microarrays. Metabolomic and metabonomic data may include small molecule metabolites, hormones, other signalling molecules, or metabolic responses obtained by mass spectrometry-based techniques, NMR spectrometry, etc. Epigenetic data may include changes in chromatin structure, such as histone modifications; transcript stability, such as DNA methylation status; nuclear organization; and small noncoding RNA species. These types of data may be obtained from high-performance liquid chromatography, bisulfite sequencing, CpG island microarrays, and chromatin immunoprecipitation-based methods. Microbiome and microbiota data may include and be obtained from direct observation methods, 16 s rRNA sequencing, 18 s sequencing, ITS gene sequencing, and molecular profiling such as metatranscriptomics, metaproteomics, metabolomics. Radiomics and digital imaging data may include and be obtained from PET, CT, histology slides and/or images, etc. Genomic data may include DNA sequencing data of coding and noncoding genomic regions of interest, and RNA sequencing data of coding and noncoding RNAs such as microRNA. Coding RNAs and gene expression data may also be obtained from single cell RNA sequencing and microarray. Noncoding RNAs may be obtained from RNA sequencing, polymerase chain reaction, and microarrays. Organoid culture assays may include healthy and disease state organoid cultures obtained from humans or animal model, such as a rodent.

Figure 7:
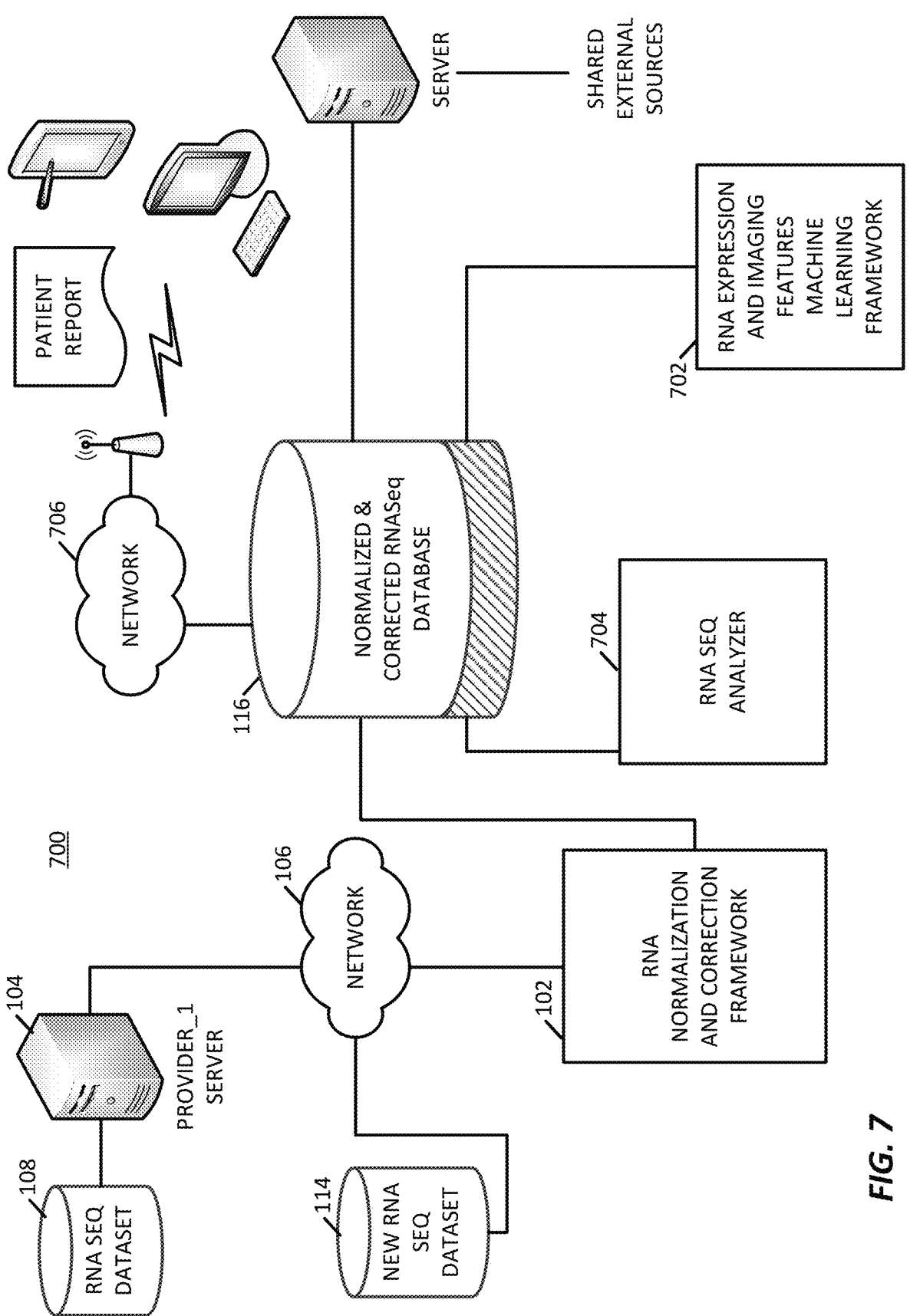
FIG. 7 is a schematic illustration of an RNA normalization and correction framework interfacing to provide normalized and corrected RNA seq data to a multi-model RNA seq, imaging features machine learning framework, and/or other framework, in accordance with an example.

FIG. 7 illustrates an example application of the gene expression normalization and correction framework 102 communicatively coupled to RNA seq analysis systems to make the standard gene expression dataset 116 available for further processing. In the illustrated example 700, the framework 102 can send the normalized and corrected dataset 116 to a RNA seq and imaging features machine learning framework 702. The framework 702 is a multi-modal framework capable of predicting immune infiltration based on integrating the normalized and corrected RNA seq data with digital imaging features. Framework 702 may be configured to predict immune infiltration in tumor samples, based on the combined data, by using a neural network framework that integrates the normalized and corrected RNA seq data neural network layer(s) with imaging feature neural network layer(s) to produce an integrated neural network output that can be used with a prediction function to produce an immune infiltration score for sample data.

In another example, the framework 102 may send the dataset 116 to another gene expression analyzer 704, providing automated processes for examining for example RNA seq data. Examples of the analyzer 704 include cancer type predictor systems, tissue/metastasis deconvolution systems, gene expression machine learning algorithms, patient report generators, and hormone receptor prediction systems. For example, the database 116, as a result of the framework 102, can be applied to the analyzer 704 which may analyze the normalized and corrected RNA seq datasets for further processing.

In some examples, the database 116 is network accessible database communicatively coupled to (or part of) a network server for providing the dataset (or access thereto) to shared external sources, such as the additional data sources described herein.

In some examples, the database 116 may provide access to the dataset for user interaction through a user terminal (as shown), a patient report generator, clinician portable device, etc., e.g., through the network 106 or through a separate network 706.

While various examples herein are described in reference to gene expression data in the form of RNA seq data, it will be appreciated that the same techniques may be applied to transcript or isoform level expression data, in a similar manner.

An example workflow implementation of the present techniques includes receiving a biological sample, such as a tissue sample, and extracting RNA from the tissue sample, where the RNA is sequenced using a protocol, such as exome-capture RNA seq. RNA seq data may then be processes to go from raw sequence data to aligned reads and expression counts, for example, using the Kallisto pipeline technique (Bray et al. Nat Biotechnol 34, 525-527 (2016)).

Of course, any number of suitable pipelines can be used. These raw expression counts are then provided to the processes in FIGS. 3-6 to develop a continuously updated and updatable reference RNA seq dataset, which can then be provided to downstream gene expression analyzers like elements 702, 704, etc.

Figure 8:
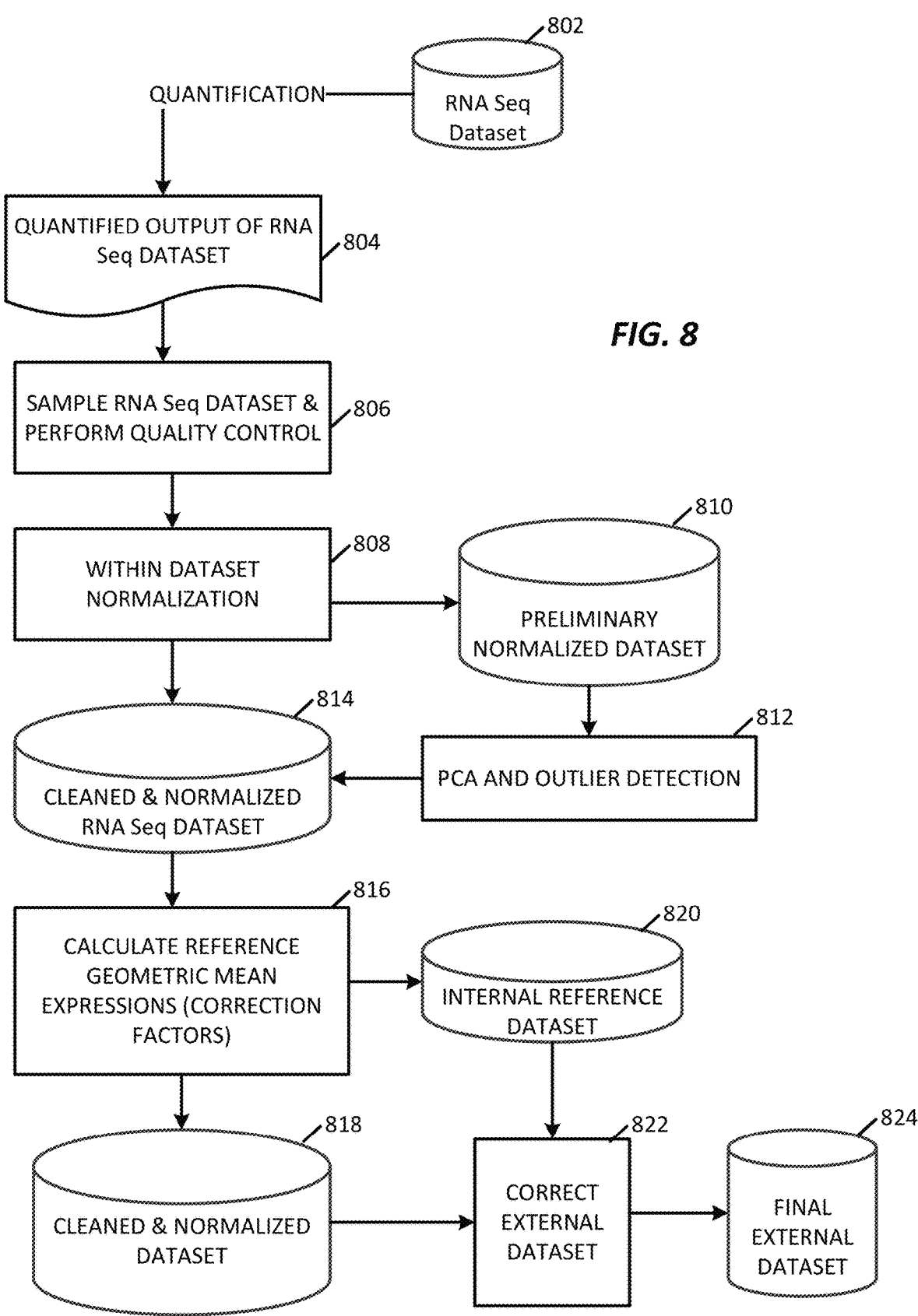
FIG. 8 illustrates an example workflow for implementing a two-step normalization process and correction process on an external gene expression dataset, in accordance with an example.

FIG. 8 provides an exemplary example workflow 800 that may be used to provide a corrected and normalized dataset. An RNA seq dataset 802 is accessed and quantified by a framework to generate a quantified output of RNA seq dataset 804.

In an example, a bioinformatics pipeline may be used to process the RNA seq data to get a raw counts RNAseq dataset for normalization and correction. The bioinformatics pipeline may receive a FASTQ file and produce a raw RNA counts file. In one exemplary bioinformatics pipeline, RNA seq dataset is accessed and a quantification using pseudo-alignment is performed. The pseudoalignment may be implemented using a transcriptome de Bruijn graph, for example. The quantification process may split a given read into k-mers (k=31 in our case) and then map each k-mer to a node in an internal database. The intersection of the k-mers is then used to quantify transcript-level expression. The output may be a near-optimal quantification of the expression of 180,053 transcripts, for example.

In an example, at a process 806, the framework performs a sampling and quality control process on a RNA seq dataset, after the bioinformatics pipeline produces an output or before the normalization steps described herein are carried out. For example, the framework may determine sequencing depth in the quantified RNA seq dataset. The framework may determine the number of expressed transcripts and the number of expressed genes. The framework may filter obvious outliers, e.g., by removing identified duplicates. In some examples, the framework filters transcripts that are off-target from a probe set.

Figure 9:
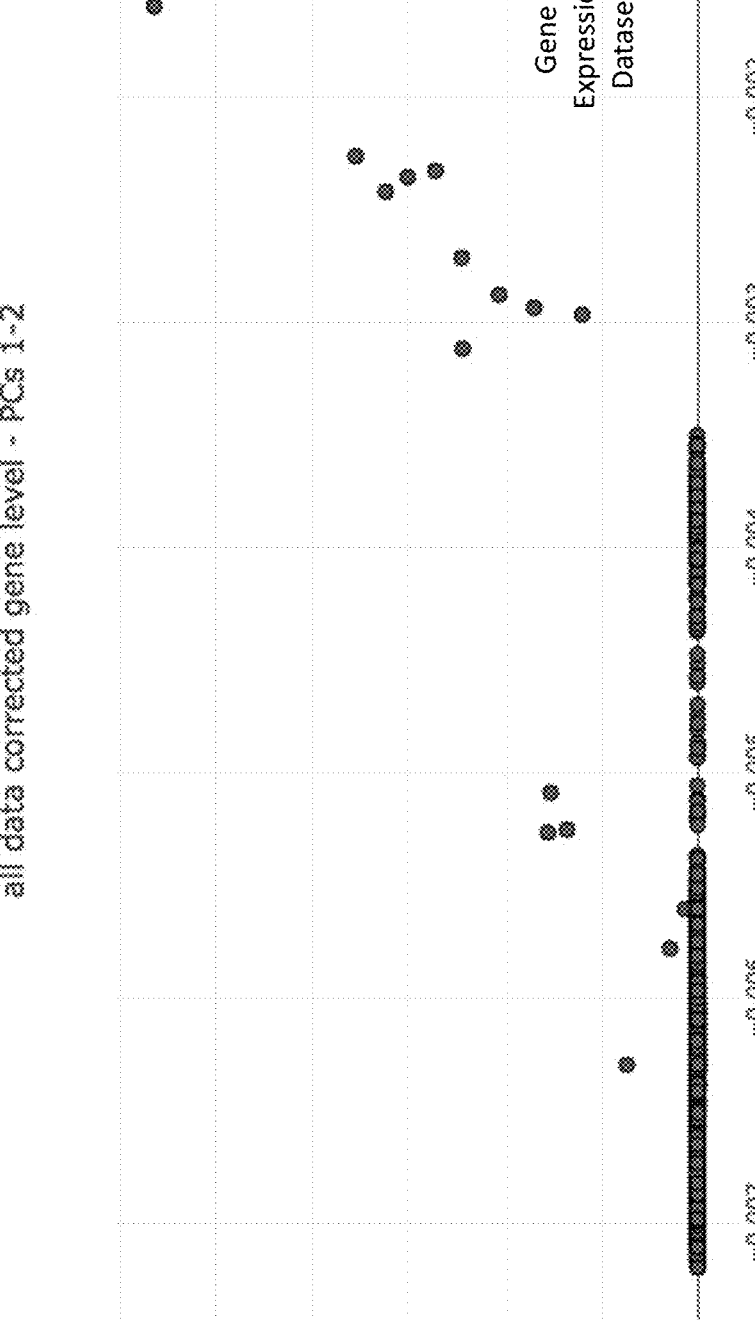
FIG. 9 is a plot of a linear mapping performed on gene expression data to identifier outliers to clean from the gene expression dataset, in accordance with an example.
Figure 10:
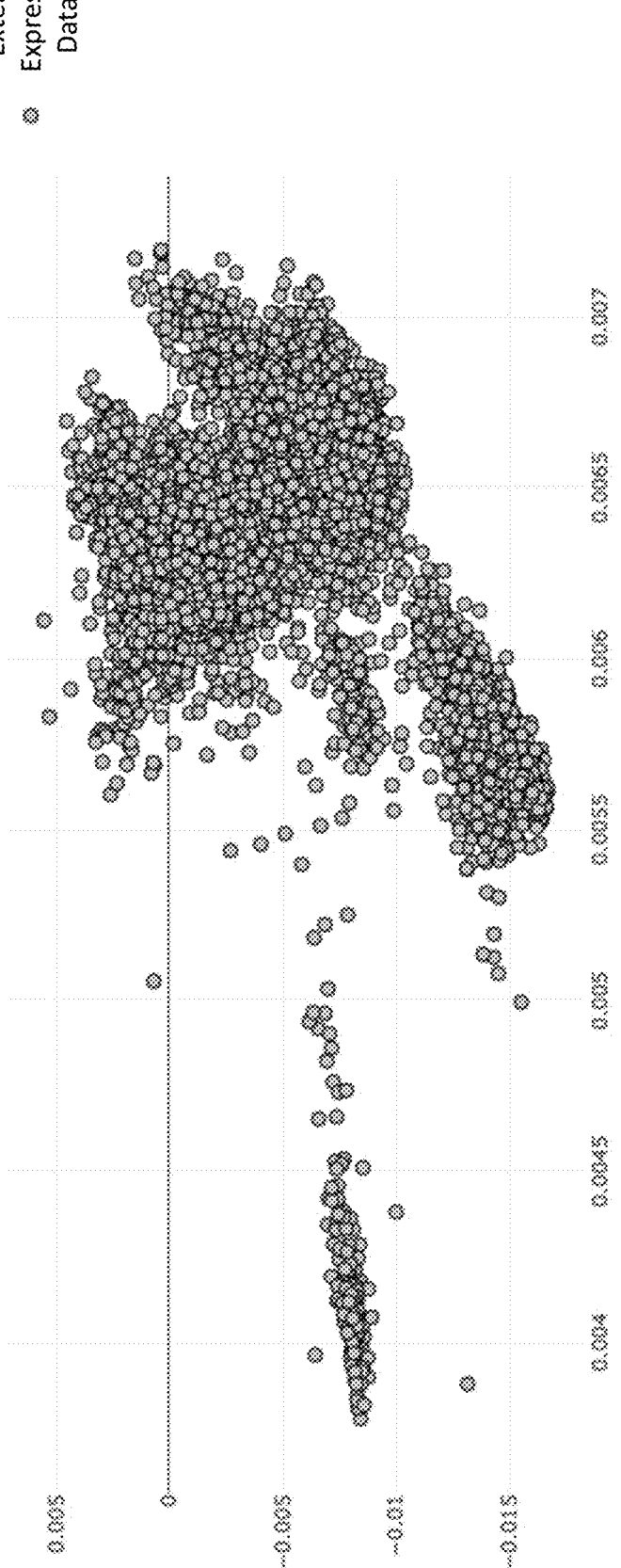
FIG. 10 is a plot of a linear mapping performed on an external gene expression data to identify outliers to clean from the external gene expression dataset, in accordance with an example.

In a series of next steps, a preliminary normalization (such as from processes 300 and 400) is performed on the RNA seq dataset. In the illustrated example, the normalization is an intra-dataset normalization, where the dataset is normalized against other data in that dataset, at a process 808. In some examples, an inter-dataset normalization is also is performed, that is, as discussed below through a normalization comparing gene expression data from different datasets. To achieve intra-dataset normalization, at the process 808, a preliminary (and temporary) normalized dataset is stored (at process 810) and, at least for the illustrated example, principal component analysis (PCA) and outlier detection is performed on that dataset, at a process 812. FIG. 9 illustrates an example, in which RNA seq data has been applied to linear mapping model and outlier gene expression data have been identified. For example, gene expression data that does not map to the x-axis (0 value) may be identified as an outlier and removed. In some examples, a threshold, cutoff value is used to identifier outliers, such as a value of ±0.1, ±0.01, ±0.005, etc. As shown in FIG. 9, outliers can be found in the data, but such outliers are resolved through the process described above. FIG. 10 illustrates an example identification of resolved outliers resulting from applying the process 800 to a dataset. A cleaned and intra-normalized RNA seq dataset 814) results, as shown in FIG. 8.

Figure 11A:
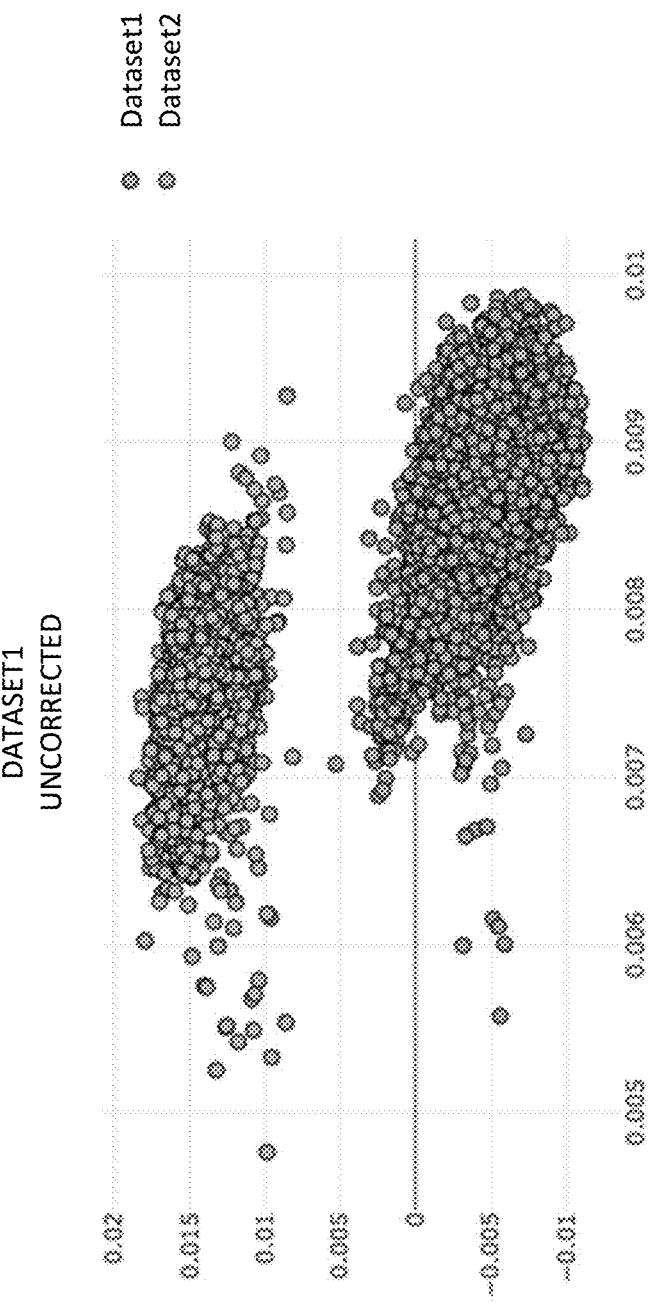
FIG. 11A is a plot of an uncorrected exemplary gene expression dataset.
Figure 11B:
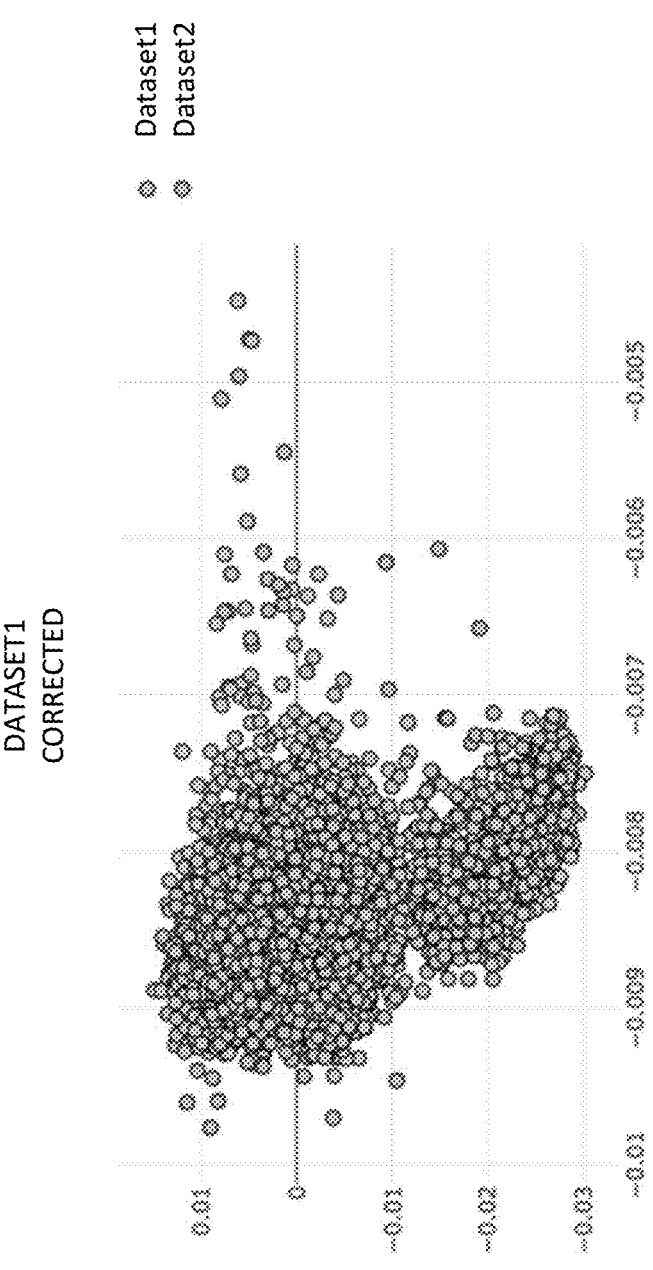
FIG. 11B is a plot of the exemplary gene expression dataset normalized and corrected, in accordance with an example.

Next, the framework implementing the process 800 (at process 816) performs a normalization and correction on the dataset 814, e.g., by determining geometric mean expressions against a reference dataset, where these expressions are correction factors for the RNA seq data. For example, the conversion factor (e.g., an intercept and a beta value for the linear mapping model), may be generated by comparison to an internal reference dataset, such as a first RNA seq dataset, i.e., an already normalized gene expression dataset. The resulting cleaned and inter-normalized dataset 820 is corrected (822) against the internal dataset 820 and a final corrected and normalized RNA seq dataset is generated (824). That final dataset may then be combined into the reference dataset and/or used for further downstream processing, such as discussed in reference to FIG. 7. FIG. 11A illustrates an example of a gene expression values in a second dataset (Dataset2) prior to application to the correction workflow 800. FIG. 11B illustrates the gene expression values of the second dataset (Dataset2) after correction and normalization, illustrating the updated dataset against a reference dataset (Dataset1). The x and y axes reflect a first and second principal component from the PCA analysis.

Figure 12:
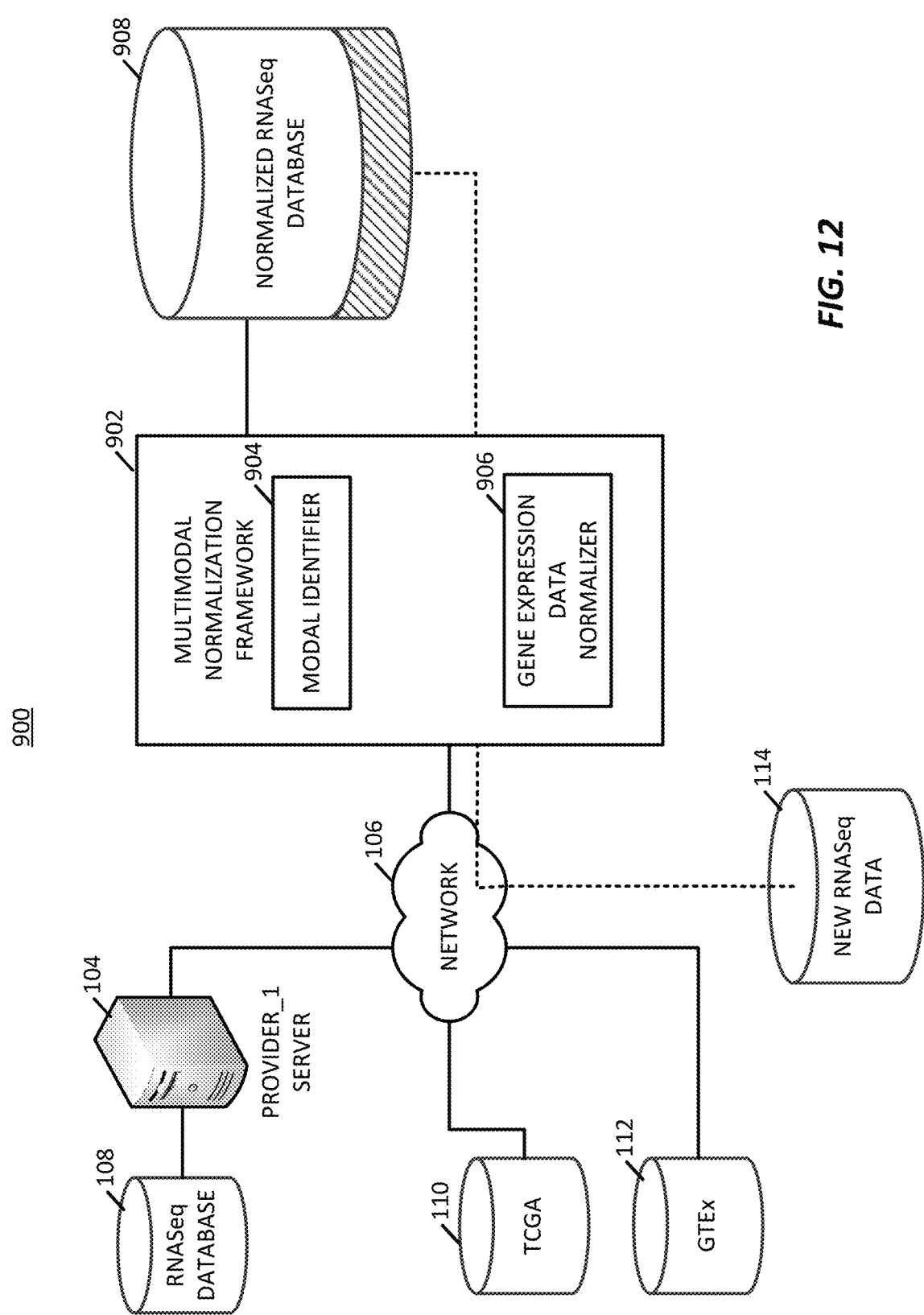
FIG. 12 is a schematic illustration of an multimodal normalization framework for normalization of gene expression data, in accordance with an example.

FIG. 12 illustrates another example system 900 for normalizing gene expression data, such as RNA seq data, and having a similar configuration to that of the system 100. A multimodal normalization framework 902 is coupled to receive gene expression data from different sources through the communication network 106, such as the health care provider computing system 104 that makes available stored gene expression data in the form of the RNA sequencing dataset 108. Other network-accessible gene expression datasets include the TCGA dataset 110 and the GTEx dataset 112. As with the normalization framework 102, the multimodal normalization framework 902 may be implemented on a computing device such as a computer, tablet or other mobile computing device, or server. The framework 902 may be implemented by any number of processors, controllers or other electronic components for processing or facilitating the RNA sequencing data analyses. In some examples, the system 900 is implemented in a broader system that includes processing and hardware for imaging feature analysis, such as analyzing features in medical imaging data, immune infiltration data analysis, DNA sequencing data analysis, organoid development analysis, and/or other modality analyses.

Figure 13:
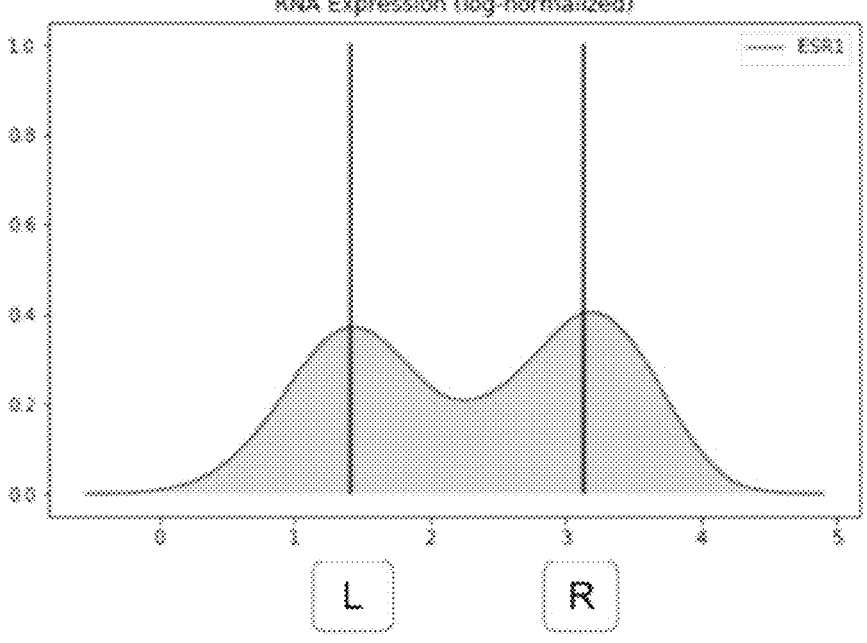
FIG. 13 is a plot of RNA expression data for ESR1, where that data exhibits a bimodal distribution prior to normalization, in accordance with an example.

The multimodal normalization framework 902 includes a modal identifier 904 and a gene expression data normalizer 906. Gene expression datasets are provided to, or accessed by, the framework 902 for normalization processing. The modal identifier 904 is configured to receive the gene expression datasets and analyze gene expression data therein to determine if any of gene expression data exhibits more than one modal expression peak. Such analysis may be performed on each gene expression data within the received dataset. Multimodal gene expression data is gene expression data that exhibits multiple modals of expression within the same population, i.e., multiple expression distribution peaks. For example, FIG. 13 illustrates gene expression data for ESR1 exhibiting a bimodal distribution with two peaks, labeled at L and R. These expression peaks may result from two different factors, such as tumor type and tissue type, which each affect ESR1 expression in this example. More generally, multimodal gene expression data can exhibit expression peaks due to a number of different factors, including, but not limited to, tissue type, cancer type, purity of tumor within sample (for example with different peaks due to different purity levels, 10%, 20%, 30%, 40%, at least 50%, at least 60%, at least 70%, at least 80%, and at least 90%), cell type (immune, lymphocyte, red blood cell, cytotoxic T cells, B cells, NK cells, macrophages, etc.), and sex of subject. Cancer types may include, but are not limited to, epithelial ovarian carcinoma, colon cancer, esophageal cancer, melanoma, endometrial cancer, and breast cancer. Other factors include batch effects, such as, differences in bioinformatics pipelines used to generate the gene expression datasets, differences in sequencing machines, dates of collection of gene expression data, and contamination of tissue.

The modal identifier 904 is configured to apply a regression technique to identify the one or more modal expression peaks in the gene expression data. In an example, the modal identifier 904 is configured as a Decision Tree Regressor. For a bimodal distribution, for example, the modal identifier 904 may implement a 2-Leaf Decision Tree Regressor that performs an auto-encoding on the gene expression data to identify two distribution peaks that minimize the mean square error (MSE) within the distribution data. The resulting two distribution peaks then are the lower and upper peak points in the gene expression data.

Figure 15:
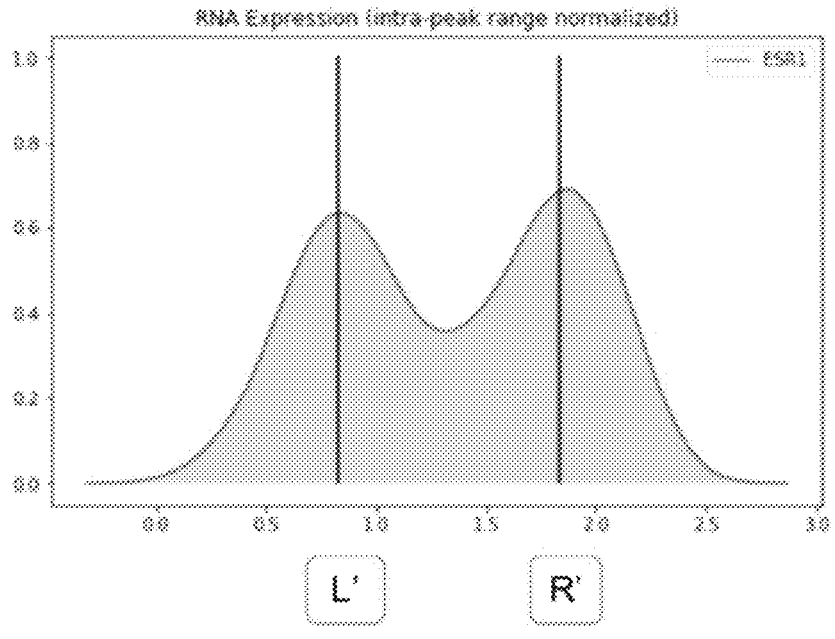
FIG. 15 is a plot of the RNA expression data for ESR1 from FIG. 13, after an intra-peak normalization of the bimodal distribution, in accordance with an example.
Figure 14:
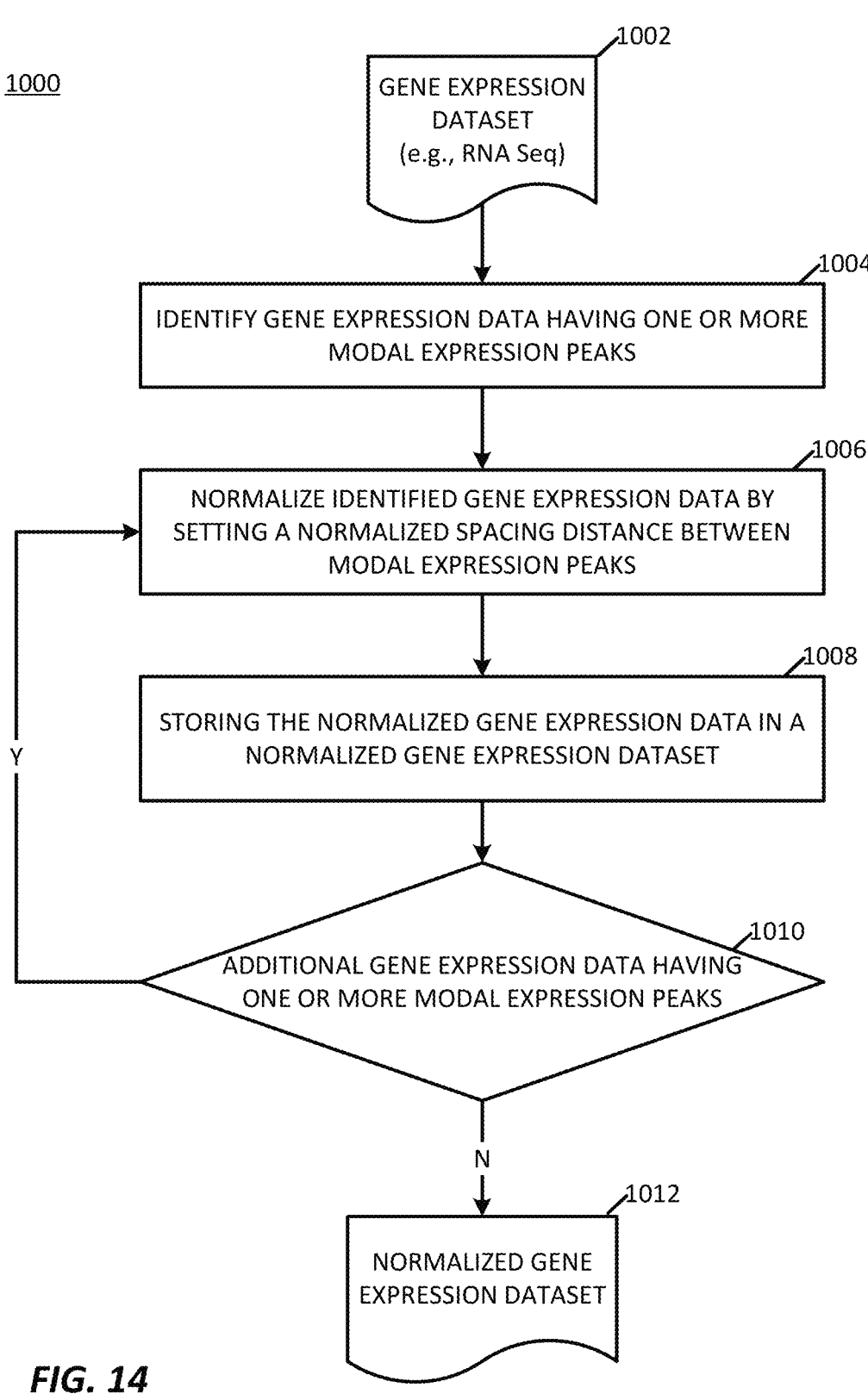
FIG. 14 is a block diagram of an example process for performing correction a multimodal gene expression data, such as the bimodal data of FIG. 13, in accordance with an example.

The gene expression data normalizer 906 receives the modal distribution peak data and gene expression data from the identifier 904 and performs a normalization on the gene expression data. FIG. 14 illustrates an example normalization process 1000 performed by the multimodal framework 902 on the gene expression data of FIG. 13. The initial gene expression data 1002, such as an RNA seq dataset, is received at the modal identifier 904, which identifies (at process 1004) one or more modal expression peaks in gene expression data within the dataset 1002. The gene expression data normalizer 906 normalizes the one or more modal expression peaks by applying a normalization rule that, in the illustrated example, normalizes a spacing distance between modal expression peaks. In the example of a bimodal distribution like that of FIG. 13, the normalizer sets a spacing distance of 1 between the identified peaks, resulting in the normalized distribution of FIG. 15. In the example of more than two distribution peaks, the normalizer 906 may set an equal spacing distance between each of the distribution peaks. In yet another example, when there are more than two distribution peaks, the normalizer 906 may establish a normalized spacing distance (e.g., a distance of 1), between the outermost peaks. Take for example, using a 2-Leaf Decision Tree Regressor approach, the normalizer 906 may be configured to optimize for the best point between auxiliary peaks (i.e., any of the peaks) to minimize overall mean-squared error in the distribution. In another example, a Decision Tree Regressor having enough leaves to match the number of peaks may be used, in which example, the normalizer 906 may be configured to perform a unit-norm between the outermost peaks, or configured to performed a unit-norm between inner-most peaks. In yet other examples of these multiple leaf Decision Tree Regressors, the normalizer 906 may be configured to proportionally space distance between detected peaks based on their individual proximity (e.g., with one far left peak and two right side peaks, the normalizer could be configured to place the left peak at −0.5, and the inner-most right peak at +0.5, and the outer most right peak at +1.0, etc). In an example, the normalizer determines the spacing distance by dividing the peak expression values (R and L) by a delta value between the R and L such that the distance between them is a normalization value, such as 1.0, resulting in normalized peaks R' and L' as shown in FIG. 15.

Figure 16:
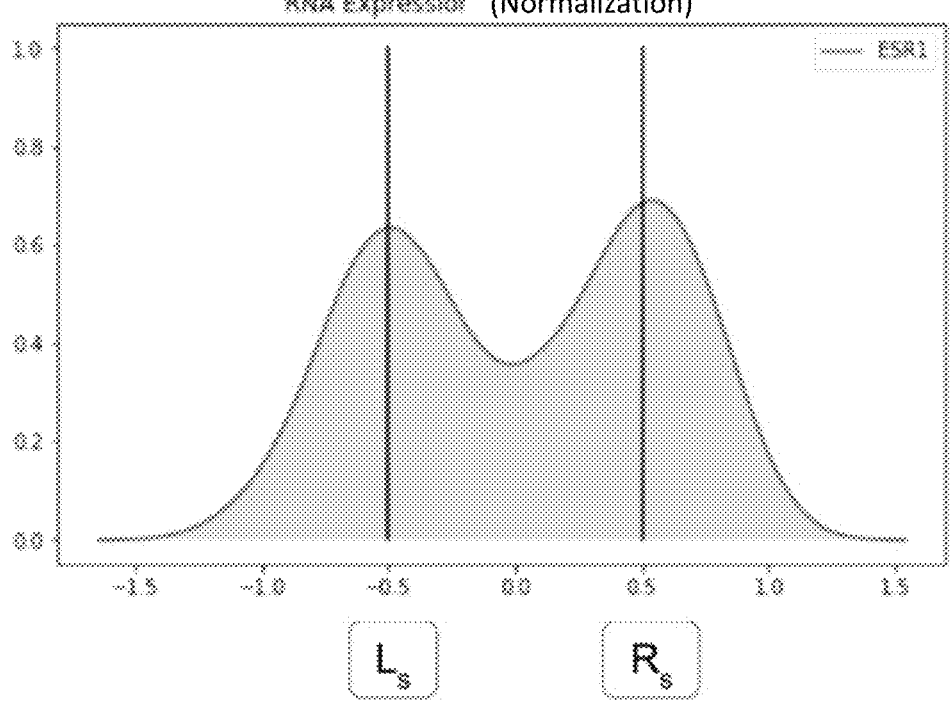
FIG. 16 is a plot of the normalized RNA expression data for ESR1 from FIG. 15, after a shift of the normalized peaks is performed, in accordance with an example.

Optionally, in some examples, the process 1006 further performs a shift on the normalized spacing gene expression data to align the peaks around a reference baseline expression value, such as a zero (0) expression. An example shift applied to the normalized bimodal gene expression data of FIG. 15 is shown in FIG. 16, resulting in shifted peaks Ls and Rs centered around a zero reference value. As a result of the shifting, over expression and under expression can be identified more readily in the gene expression data.

The normalized gene expression data is then stored in a normalized gene expression dataset at process 1008. In some examples, the process 1008 may remove the un-normalized gene expression data from the dataset 1002 and replace that data with the normalized gene expression data. In some examples, the normalized gene expression data may be added to the dataset 1002. In yet other examples, the normalized gene expression data is added to a separate normalized gene expression dataset 908 (shown in FIG. 12).

This normalization may be applied across all gene expression data within the dataset 1002 to generate a normalized gene expression dataset that aligns each of the different gene expression data within the dataset. At a process 1010, the framework 902 determines if there is additional gene expression data within the dataset to be normalized, and if so the process 900 repeats applying the distribution peak spacing normalization rule (and optional shifting rule) to each subsequent gene expression data, until a completed normalized gene expression dataset 1012 (e.g., dataset 908) is formed.

Figure 17A:
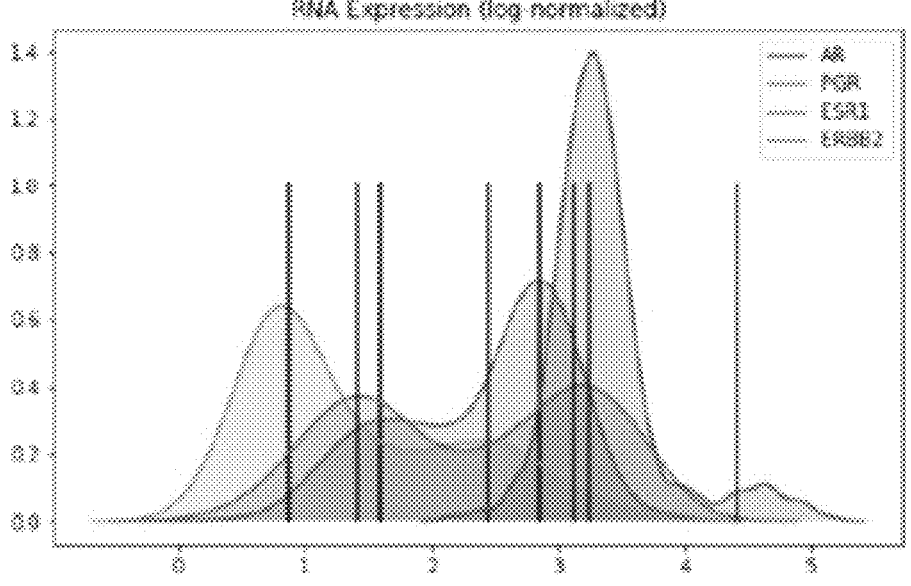
FIG. 17A is a plot of bimodal RNA expression data for multiple different genes (AR, PGR, ESR1, ERBB2), prior to normalization.
Figure 17B:
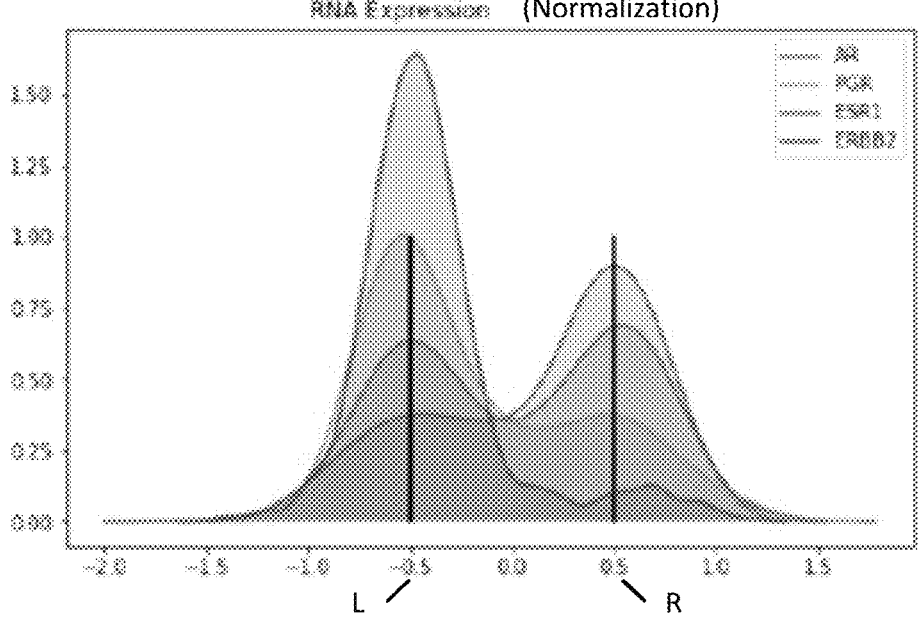
FIG. 17B is a plot of that RNA expression data after normalization showing aligned peaks for the bimodal distributions of the data, in accordance with an example.

FIG. 17A shows example gene expression data corresponding to four different genes (AR, PGR, ESR1, and ERBB2) prior to normalization. Each of the gene expression data exhibits bimodal distribution peaks, for example, resulting from different expression of the gene in different tissue. FIG. 17B illustrates the gene expression data after normalization applied by the process 1000 of the framework 902. As shown, the normalized gene expression data has the bimodal distribution peaks aligned, L and R, and centered around a zero reference expression.

Figure 18:
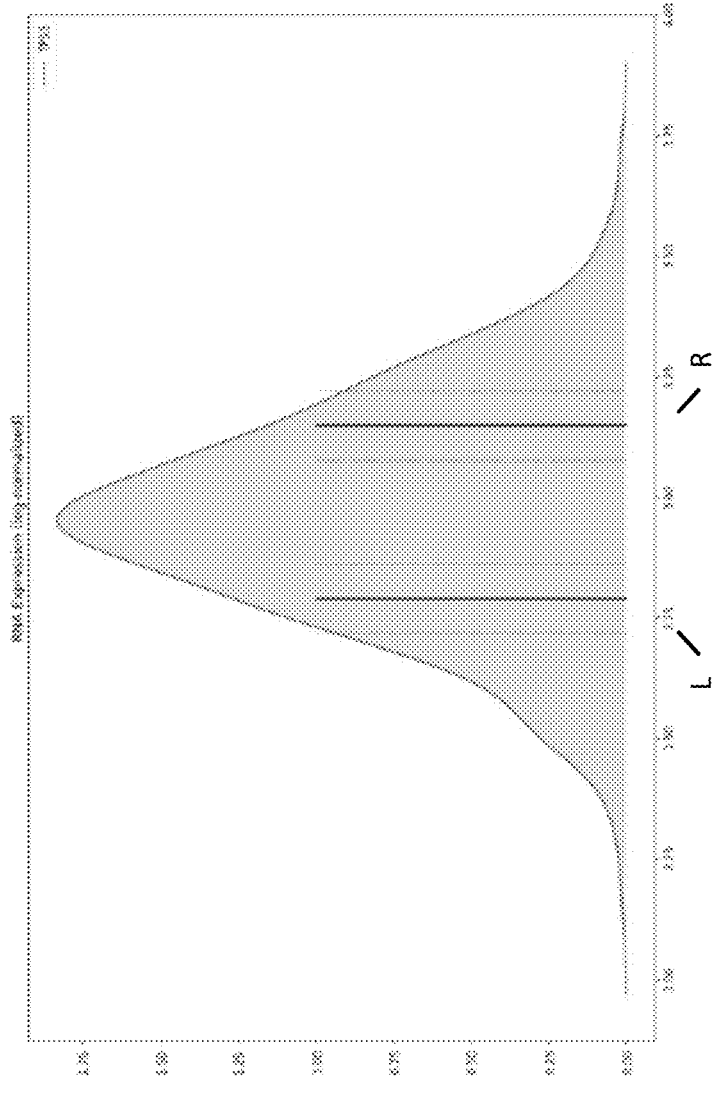
FIG. 18 is a plot of the RNA expression data for TP53 which exhibits a uni-modal distribution, showing a bimodal peak normalization process in progress, in accordance with an example.
Figure 19A:
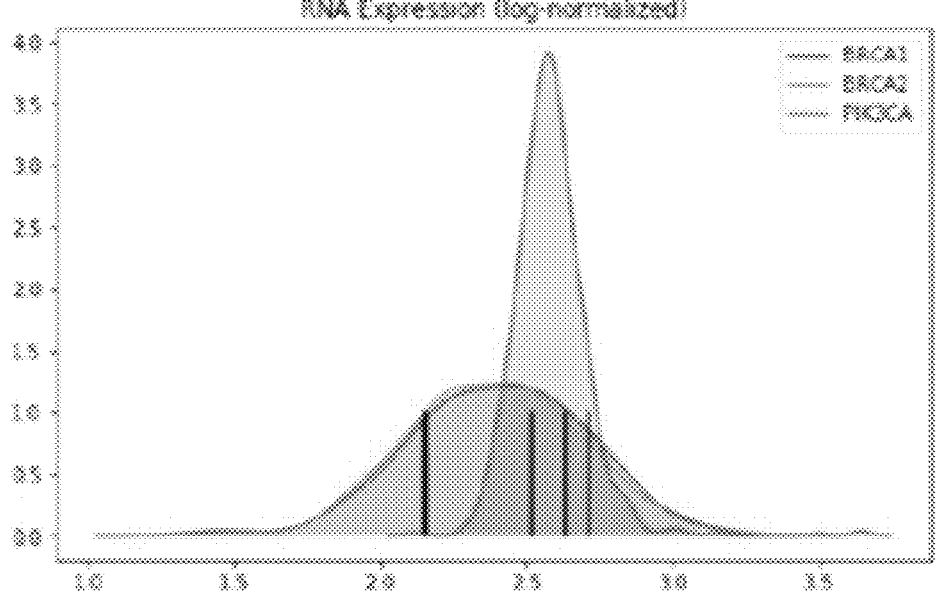
FIG. 19A is a plot of uni-modal RNA expression data for multiple different genes (BRCA1, BRCA2, PIK3CA), prior to normalization.
Figure 19B:
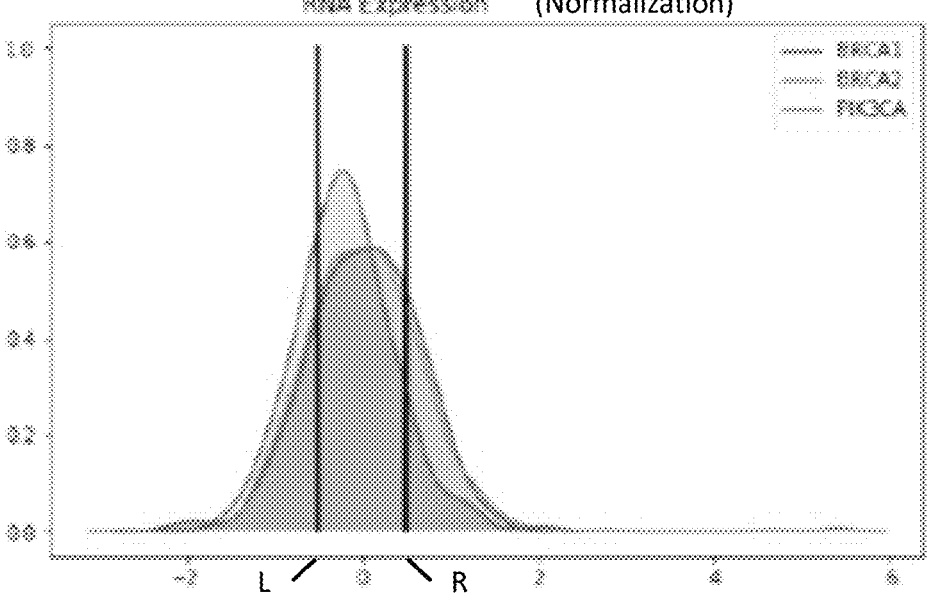
FIG. 19B is a plot of that uni-modal RNA expression data after normalization showing alignment resulting a bimodal peak normalization process, in accordance with an example.

The normalization of process 1000 may be applied to gene expression data exhibiting uni-modal expression distribution, such as shown in FIG. 18. With the modal identifier 904 configured as a bimodal peak identifier (e.g., a 2-Leaf Distribution Tree Regressor), the framework 902 identifies imposed "peaks" on the distribution as the locations on the distribution that minimize the mean-square error for the distribution. With these imposed "peaks" identified, the normalizer 906 may perform a transformation on the data to establish a normalized spacing between these peaks and another, linear transformation to shift the distribution. FIG. 19A illustrates uni-modal gene expression data for genes BRCA1, BRCA2, and PIK3CA prior to normalization by the process 1000, and FIG. 19B illustrates the corresponding normalized gene expression data after the process 1000.

Figures 20A, 20B:
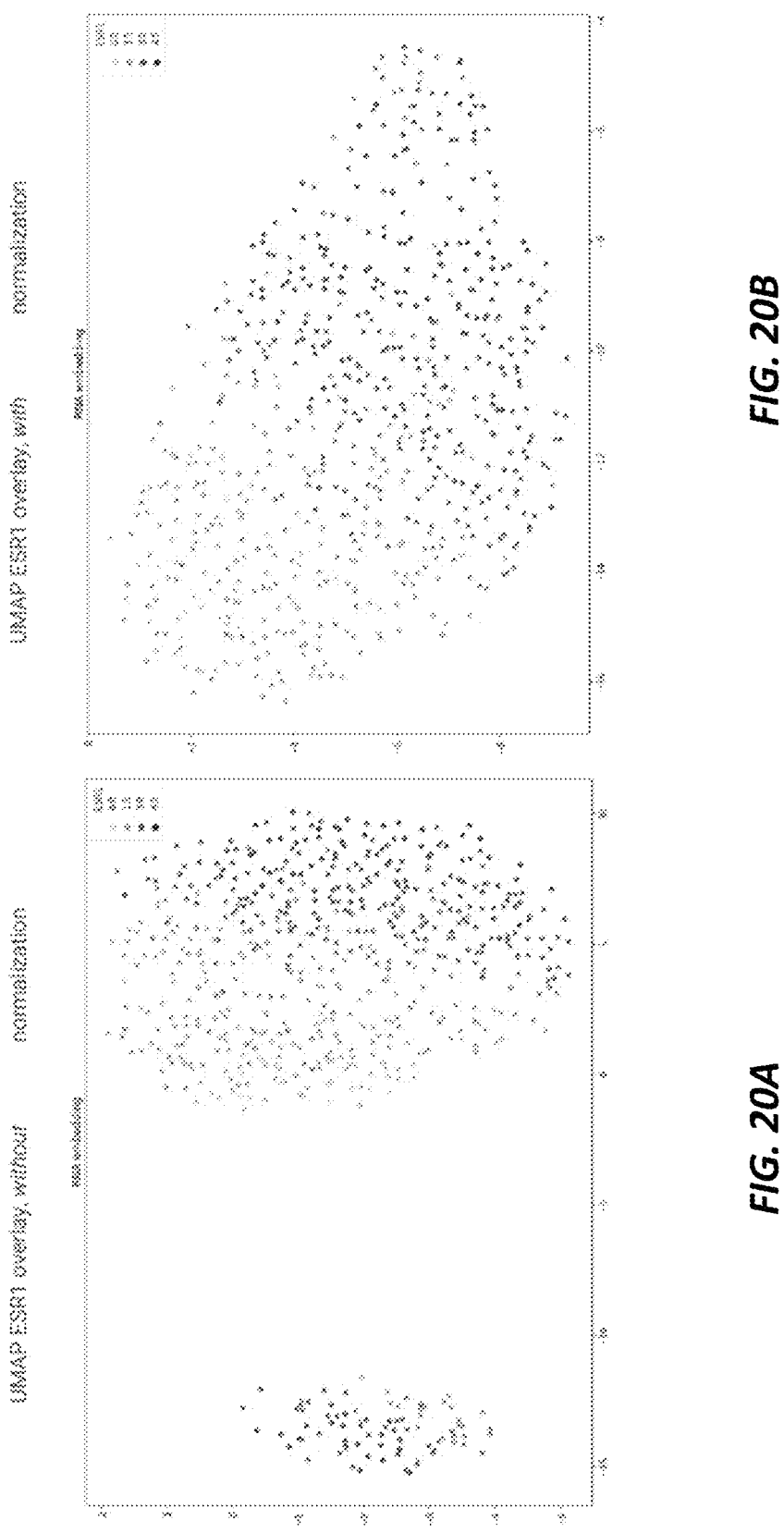
FIG. 20A is a plot of Uniform Manifold Approximation and Projection (UMAP) of ESR1 gene expression data prior to normalization.
FIG. 20B is a plot of UMAP for that RNA expression data after normalization, in accordance with an example.

By identifying and normalization multi-modal gene expression data within a dataset, such as within the RNA transcriptome, an gene sequence analyzer, such as the RNA Seq analyzer 704 in FIG. 7, is able to generate more accurate gene expression data for more accurate identification of population groups, suggested treatments, biomarker discovery, molecular sub-type clustering and identification, population clustering visualization, etc. For example, with a modal identifier configured as a bimodal identifier, a normalized gene expression dataset is formed where one of the expression factors may be isolated out from affecting analysis. FIG. 20A illustrates a Uniform Manifold Approximation and Projection (UMAP) plot of ESR1 gene expression data prior to normalization. The UMAP plot shows a large distance between two different clusters, A and B: one (A) that corresponds to expression data captured from a first tissue type, in this case liver tissue, and another (B) that corresponds to a second tissue type, breast tissue. The distances between the clusters demonstrates that any attempt to use the UMAP to identify ESR1 expression is tissue dependent. FIG. 20B illustrates another UMAP plot but after normalization, where tissue dependence, as shown, has been removed from the data. The UMAP visualization of the gene expression data is achieved computationally faster or more accurately with removed tissue using the normalization process. The same computational speed efficiency and tissue removal accuracy can be achieved in other visualization techniques, including principal component analysis (PCA) and t-Distributed Stochastic Neighbor Embedding (t-SNE). Indeed, the computationally efficiencies are considerable for visualizations such as UMAP, which is generally faster than t-SNE and generally is more accurate than PCA. With the normalization techniques herein, a RNA Seq analyzer can generate more accurate gene expression data reports, as a result. More generally, with the normalized data, the RNA Seq analyzer can more accurately identify samples based on expression values for ESR1, with the tissue dependence removed. Moreover, the RNA Seq analyzer can remove tissue dependence (or any other factor being considered against cancer in a bimodal analysis configuration) across all gene expression data. Thus, with the present techniques, gene expression data for different genes (and thus for different cancer types) can be normalized to be tissue independent, thereby allowing an RNA Seq analyzer to more quickly and more accurately identify cancer type for a subject irrespective of whether the tissue sample is from a primary site of cancer or a secondary malignant cancer site.

In some aspects, the GC bias length may be normalized in order to more effectively permit comparison of gene expression in a single sample. In some aspects, the read depth and gene length may be normalized to more effectively permit comparison of gene expression across multiple samples. The normalization may be performed on a set of paired-end RNA reads or a set of single-end RNA reads. The normalization may be performed on RNA-seq data or other RNA data that is generated using methods known in the art.

In one aspect, a normalized set of RNA may be utilized in connection with expression calling. Prior to normalization, samples may be biased by the depth of sequencing.

Comparison of transcriptome measures from among samples may be biased by depth of sequencing. Normalization permits comparison of expression levels of a single gene across samples. For instance, when calling overexpression of a gene, the overexpression may be made with respect to expression of other samples. As an example, sequencing of 20 breast cancer specimens at a depth of 20 million reads may result in 100 reads of the ESR1 estrogen receptor gene for each sequenced specimen. Sequencing of another 20 breast cancer specimens at patients at a depth of 40 million reads may result in 200 reads of the ESR1 estrogen receptor gene for each sequenced specimen. Normalizing the two data sets permits normalization of the read count across the two data sets.

As another example, a normalized RNA data set may be utilized in connection with a tumor of unknown origin predictor model. The model may have to learn certain parameters for each gene. To apply those parameters to each gene among many different specimens, it is preferred that the gene expression value look the same across patients. If the model, for example, applies an estrogen level read depth by a factor of two, the model will be biased by the read depth. Where the tumor of unknown origin predictor model is formed as, for example, a linear model, each gene is provided with a weight by which the associated expression level is multiplied.

Figure 21:
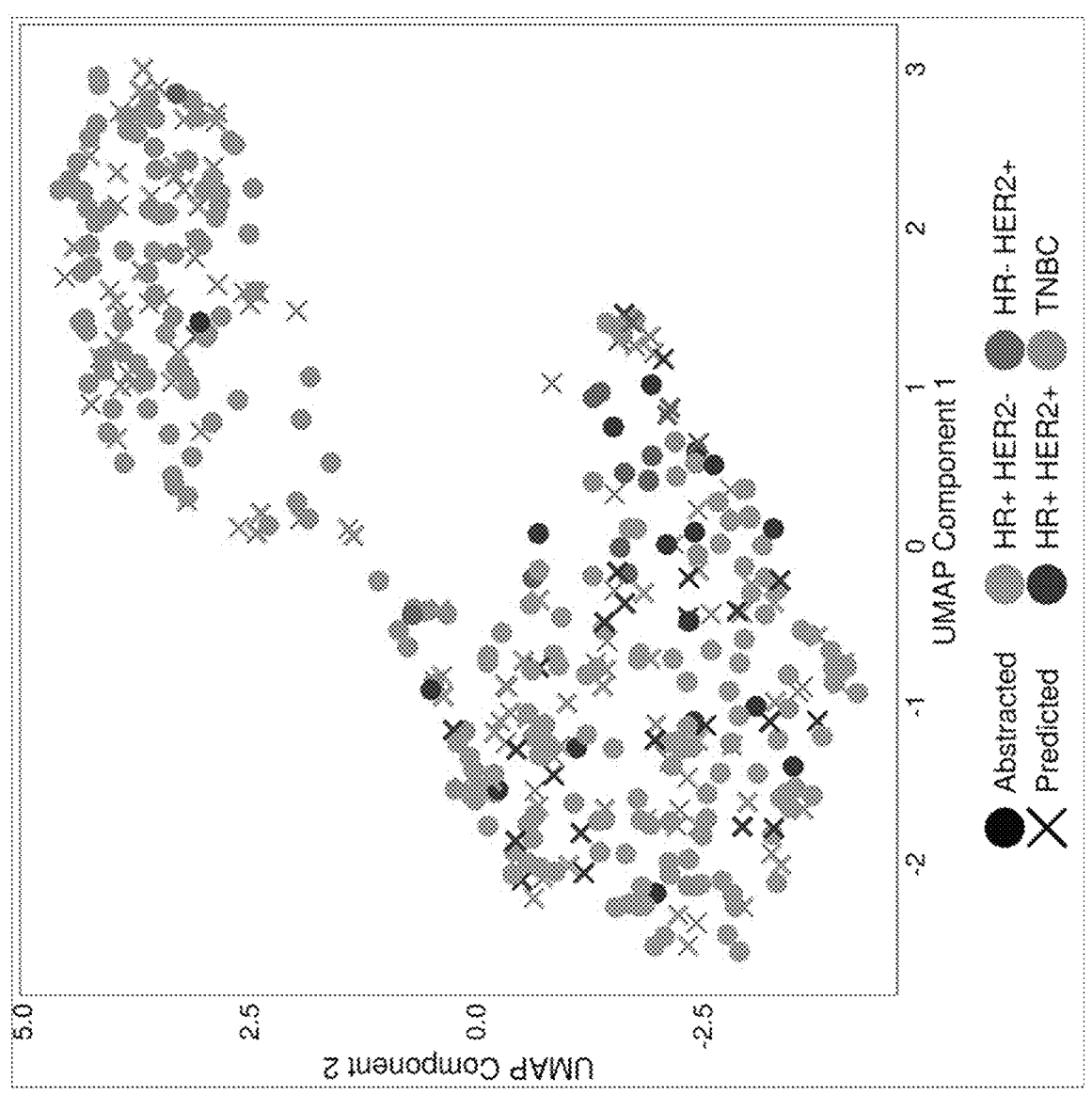
FIG. 21 displays a UMAP plot of a cohort of patient specimens with one cluster of triple negative breast cancer specimens.

As another example, a normalized RNA data set may be utilized in connection with one or more methods to cluster samples in order, for instance, to identify disease subtypes. By comparing RNA expression levels among samples, clustering may be utilized to suggest those samples that are most similar to one another. In some embodiments, the normalization may be limited to normalizing read depth among samples. In other embodiments, the normalization may be limited to normalizing read depth and GC content. In other embodiments, the normalization may comprise normalization of read depth, GC content, and gene length. In an example, a set of normalized RNA transcriptomes may be matched with IHC staining information to identify cohorts of specimens with HER2+ status. For example, in a cohort of 400 specimens, 300 of the specimens may have an associated IHC stain and 100 do not. For the 100 that do not, an IHC prediction model may be used to predict the IHC status and then UMAP clustering may be utilized to cluster the specimens. Specimens with a normalized expression of ESR1 (for ER) or PGR (for PR) or ERBB2 (for HER2) above a pre-defined threshold may be stratified. In one embodiment the threshold is 2.5. Some specimens may have data available for ER, PR, and HER2 in which case the specimen is displayed in FIG. 21 as a circle. Other specimens may not have data available for ER, PR, or HER2 in which case the specimen may be displayed in FIG. 21 as an X mark.

As another example, a RNA normalization may be utilized to compare gene expression levels relative to each other within a sample. In some aspects, GC bias may be present in gene length. For example, if gene A is 100 kb and gene B is 200 kb, the same number of RNA molecules may exist for gene. However, gene B would have twice the counts of gene A because gene B's RNA molecule is twice the size. During PCR amplification in library prep, if a fragment has about 50% GC content it will have a first level of amplification. If, on the other hand, the GC content deviates significantly from 50% GC content, it will not amplify as well. For example, the GC content may deviate significantly if it has 80% content. A first gene with a first percentage GC content closer to 50% GC content and a second gene with a second percentage GC content that significantly deviates from the first gene content can have the same number of RNA molecules in the cell but the first GC content gene will have been amplified more than the second GC content gene during PCR amplification. RNA normalization of GC content may be utilized within a sample to compare the GC content of a first gene to the GC content of a second gene.

In another aspect, RNA normalization may be utilized in connection with a drug response model. In an exemplary drug response model, the model may multiply each gene expression value by a number the model has learned. The model may be trained on read depth normalized data and may be utilized to predict drug response using RNA expression information that has been normalized in a like fashion to the training RNA expression information. For instance, the drug response model may take the form $y=a1\times1+a2\times2+ \ldots +an\times n$, where a1, a2, . . . , an are weights and x1, x2, . . . , xn are genes. If y<1 then the model may be set to not respond to the particular drug that is the focus of the model. If y>1 the model may be set to respond to the particular drug that is the focus of the model.

In another aspect, RNA normalization may be utilized in connection with an assessment of pathway activity. For example, RNA expression data may be normalized as to GC content and length. For example, in the field of single sample gene set enrichment analysis, each gene's transcription levels may be normalized to adjust for GC bias in order to develop a ranked list of normalized gene expression values.

The expression values of a pre-defined gene list, reflecting genes known to be associated with a pathway, may be examined in order to identify whether the genes in associated with the pathway are overexpressed, underexpressed, or a combination thereof that is relevant to the pathway. In this way, a set of normalized RNA data may be utilized to identify an activated pathway in the specimen.

In another aspect, RNA normalization may be utilized in connection with a comparison of expression levels of a given gene among a set of patients. For instance the read depth may be normalized in order to compare the expression levels of a BRAF mutation among patients.

In another aspect, RNA normalization may be utilized in connection with analysis of RNA expression information in order to identify potential sample swaps or input missing data. For example, a model $y=a1\times1+a2\times2+ \ldots +an\times n$, where a1, a2, . . . , an are weights and x1, x2, . . . , xn are genes may be trained on a set of RNA expression information and the patient's gender. Read count and GC count may be normalized across the applicable RNA data set. By inputting the normalized RNA expression information of a new specimen, normalized in a like fashion to the training data set, it is possible to determine whether the specimen is from a male patient or a female patient. If the gender of the patient from whom the specimen was received was reported as male, but the gender analysis indicates the specimen came from a female person, the disparity would indicate a quality control process to confirm whether the specimen was the result of a sample swap, was taken from a patient who had a gender reassignment, or was from a patient whose gender was mis-identified in the patient's electronic health record.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternative embodiments, using either current technology or technology developed after the filing date of this application.

What is claimed:

1. A computer-implemented method for measuring gene expression based on RNA expression data from disparate samples, comprising:

obtaining, via one or more processors, (i) an experimental RNA sequence dataset for one or more genes from one or more experimental samples and (ii) a reference RNA sequence dataset for one or more genes from one or more reference samples, wherein the experimental RNA sequence dataset comprises experimental gene length data, experimental guanine-cytosine (GC) content data, and experimental depth of sequencing data for each of the one or more genes from the one or more experimental samples, wherein the reference RNA sequence dataset comprises reference gene length data, reference guanine-cytosine (GC) content data, and reference depth of sequencing data for each of the one or more genes from the one or more reference samples, wherein at least one of the one or more experimental samples and at least one of the one or more reference samples are not from identical tissue type and/or RNA selection method;

generating, via the one or more processors, normalized RNA sequence data to reduce biases introduced by sample preparation by normalizing the experimental depth of sequencing data for the experimental RNA sequence dataset by:

(a) determining, via the one or more processors, a set of ratios of the experimental depth of sequencing data to a geometric mean of the reference depth of sequencing data, wherein each ratio of the set of ratios represents a respective one of the one or more genes;

(b) determining, via the one or more processors, a size factor as a median of the set of ratios; and (c) converting, via the one or more processors, the experimental RNA sequence dataset into a normalized RNA sequence dataset using the size factor;

generating, based on the normalized RNA sequence dataset, a gene expression status of the one or more genes of the one or more experimental samples;

generating, via the one or more processors, at least one conversion factor based on a comparison of the normalized RNA sequence dataset to the reference RNA sequence dataset by determining a statistical mapping between sample data of the normalized RNA sequence dataset and sample data of the reference RNA sequence dataset;

integrating, via the one or more processors, the normalized RNA sequence dataset into the reference RNA sequence dataset, by using the at least one conversion factor, to form a uniform gene expression database of comparable gene expression data from the disparate samples; and enabling a multi-modal machine learning framework to access the uniform gene expression database and integrate the comparable gene expression data with imaging features to generate a neural network output used for analyzing biological samples.

2. The computer-implemented method of claim 1, further comprising:

normalizing the experimental gene length data for each gene of the one or more genes from the one or more experimental samples; and normalizing the experimental GC content data for each gene of the one or more genes from the one or more experimental samples.

3. The computer-implemented method of claim 2, wherein normalizing the experimental gene length data comprises using a quantile normalization procedure.

4. The computer-implemented method of claim 2, wherein normalizing the experimental GC content data comprises using a quantile normalization procedure.

5. The computer-implemented method of claim 1, further comprising:

normalizing, via the one or more processors, the experimental RNA sequence dataset by applying a Reads Per Kilobase Million (RPKM) normalization, a Fragments Per Kilobase Million (FPKM) normalization, or a Transcripts Per Kilobase Million (TPM) normalization.

6. The computer-implemented method of claim 1, wherein the experimental RNA sequence dataset is a raw dataset.

7. The computer-implemented method of claim 1, wherein the experimental RNA sequence dataset is a Cancer Genome Atlas (TCGA) dataset.

8. The computer-implemented method of claim 1, wherein the experimental RNA sequence dataset is a Genotype-Tissue Expression (GTEx) dataset.

9. The computer-implemented method of claim 1, wherein determining the statistical mapping comprises determining a linear mapping model between the sample data of the normalized RNA sequence dataset and the sample data of the reference RNA sequence dataset, the computer-implemented method further comprising:

determining an intercept and a beta value for the linear mapping model; and determining the at least one conversion factor using the statistical mapping from the intercept and the beta value.

10. The computer-implemented method of claim 1, wherein generating the at least one conversion factor comprises:

(i) for at least one of the one or more genes, obtaining the sample data from the normalized RNA sequence dataset and obtaining the sample data from the reference RNA sequence dataset;

(ii) determining a linear mapping model between the sample data of the normalized RNA sequence dataset and the sample data of the reference RNA sequence dataset;

(iii) determining an intercept and a beta value for the linear mapping model;

(iv) performing (i)-(iii) a plurality of times for the at least one of the one or more genes to generate a pool of values; and (v) determining a gene specific conversion factor from a mean intercept and a mean beta value based on the pool of values.

11. The computer-implemented method of claim 1, wherein an embedding is visualized using a dimensionality reduction technique.

12. The computer-implemented method of claim 1, wherein the tissue type is fresh frozen (FF) or formalin fixed, paraffin embedded (FFPE).

13. The computer-implemented method of claim 1, wherein the RNA selection method is exon capture or poly-A RNA selection.

14. A computing device comprising one or more memories and one or more processors configured to:

obtain, via the one or more processors, (i) an experimental RNA sequence dataset for one or more genes from one or more experimental samples and (ii) a reference RNA sequence dataset for one or more genes from one or more reference samples, wherein the experimental RNA sequence dataset comprises experimental gene length data, experimental guanine-cytosine (GC) content data, and experimental depth of sequencing data for each of the one or more genes from the one or more experimental samples, wherein the reference RNA sequence dataset comprises reference gene length data, reference guanine-cytosine (GC) content data, and reference depth of sequencing data for each of the one or more genes from the one or more reference samples, and wherein at least one of the one or more experimental samples and at least one of the one or more reference samples are not from identical tissue type and/or RNA selection method;

generate, via the one or more processors, normalized RNA sequence data to reduce biases introduced by sample preparation by normalizing the experimental depth of sequencing data for the experimental RNA sequence dataset by:

(a) determining, via the one or more processors, a set of ratios of the experimental depth of sequencing data to a geometric mean of the reference depth of sequencing data of the reference RNA sequence dataset, wherein each ratio of the set of ratios represents a respective one of the one or more genes;

(b) determining, via the one or more processors, a size factor as a median of the set of ratios; and (c) converting, via the one or more processors, the experimental RNA sequence dataset into normalized RNA sequence dataset using the size factor;

generate, based on the normalized RNA sequence dataset, a gene expression status of the one or more genes of the one or more experimental samples;

generate, via the one or more processors, at least one conversion factor based on a comparison of the normalized RNA sequence dataset to the reference RNA sequence dataset by determining a statistical mapping between sample data of the normalized RNA sequence dataset and sample data of the reference RNA sequence dataset;

integrate, via the one or more processors, the normalized RNA sequence dataset into the reference RNA sequence dataset, by using the at least one conversion factor, to form a uniform gene expression database of comparable gene expression data from the disparate samples; and enable a multi-modal machine learning framework to access the uniform gene expression database and integrate the comparable gene expression data with imaging features to generate a neural network output used for analyzing biological samples.

15. The computing device of claim 14, wherein the one or more processors are configured to generate the normalized RNA sequence data by being configured to:

normalize the experimental gene length data for the one or more genes from the one or more experimental samples; and normalize the experimental GC content data for the one or more genes from the one or more experimental samples.

16. The computing device of claim 14, wherein the one or more processors are configured to determine the statistical mapping by being configured to determine a linear mapping model between the sample data of the normalized RNA sequence dataset and the sample data of the reference RNA sequence dataset, the one or more processors being further configured to:

determine an intercept and a beta value for the linear mapping model; and determine the at least one conversion factor using the statistical mapping from the intercept and the beta value.

* * * * *